(12) United States Patent
Leary

(10) Patent No.: US 10,279,119 B2
(45) Date of Patent: May 7, 2019

(54) SAFETY SYRINGE AND METHODS FOR ADMINISTRATION OF A MEDICAMENT DOSE BY SUBJECT WEIGHT

(71) Applicant: Brell Medical Innovations, LLC, Henrico, VA (US)

(72) Inventor: Jeffrey M. Leary, Henrico, VA (US)

(73) Assignee: Brell Medical Innovations, LLC, Henrico, VA (US)

( * ) Notice: Subject to any disclaimer, the term of this patent is extended or adjusted under 35 U.S.C. 154(b) by 116 days.

(21) Appl. No.: 15/266,023

(22) Filed: Sep. 15, 2016

(65) Prior Publication Data

US 2017/0000952 A1 Jan. 5, 2017

Related U.S. Application Data

(62) Division of application No. 14/966,097, filed on Dec. 11, 2015, now Pat. No. 9,474,864.
(Continued)

(51) Int. Cl.
*A61M 5/31* (2006.01)
*A61M 5/315* (2006.01)

(52) U.S. Cl.
CPC ...... *A61M 5/31555* (2013.01); *A61M 5/3129* (2013.01); *A61M 5/3135* (2013.01);
(Continued)

(58) Field of Classification Search
CPC ...... A61M 2005/3126; A61M 5/31525; A61M 2005/3125; A61M 5/31555
See application file for complete search history.

(56) References Cited

U.S. PATENT DOCUMENTS 4,209,023 A * 6/1980 Layton .................... A61B 5/03
600/561
4,493,348 A 1/1985 Lemmons
(Continued)

FOREIGN PATENT DOCUMENTS

WO WO2004/020028 A1 3/2004
WO WO2008/016381 A1 2/2008
WO WO2013/116353 A1 8/2013

OTHER PUBLICATIONS

Bates, D. W., et al., "Incidence of Adverse Drug Events and Potential Adverse Drug Events," Journal of the American Medical Association, Jul. 5, 1995, vol. 274, No. 1, pp. 29-30.
(Continued)

*Primary Examiner* — Edelmira Bosques
(74) *Attorney, Agent, or Firm* — ReavesColey PLLC

(57) ABSTRACT

An apparatus includes a syringe body and a plunger. The syringe body defines a volume configured to contain a medicament. A proximal end portion of the syringe body includes an engagement portion, and a distal end portion of the syringe body includes a delivery tip. A side wall of the syringe body includes a transparent window. The plunger has a distal end portion configured to move within the volume of the syringe body to convey the medicament. An engagement portion of the plunger is configured to interface with the engagement portion of the syringe body to limit rotation of the plunger about a longitudinal axis of the plunger. An outer surface of the plunger includes a series of indicia, at least one which is visible through the transparent window.

20 Claims, 14 Drawing Sheets

Related U.S. Application Data

(60) Provisional application No. 62/092,234, filed on Dec. 15, 2014.

(52) U.S. Cl.
CPC .... *A61M 5/31505* (2013.01); *A61M 5/31525* (2013.01); *A61M 5/31526* (2013.01); *A61M 5/31561* (2013.01); *A61M 5/31568* (2013.01); *A61M 5/31586* (2013.01); *A61M 2005/3114* (2013.01); *A61M 2005/3126* (2013.01); *A61M 2205/583* (2013.01); *A61M 2205/6009* (2013.01)

(56) References Cited

U.S. PATENT DOCUMENTS

| | | |
|---|---|---|
| 4,750,373 A | 6/1988 | Shapiro |
| 4,865,591 A | 9/1989 | Sams |
| 5,010,656 A | 4/1991 | Broselow |
| 5,328,486 A | 7/1994 | Woodruff |
| 5,376,081 A | 12/1994 | Sapienza |
| 5,667,495 A | 9/1997 | Bitdinger et al. |
| 6,132,416 A | 10/2000 | Broselow |
| 6,382,204 B1 | 5/2002 | Jansen et al. |
| 6,530,906 B2 | 3/2003 | Hu |
| 6,764,469 B2 | 7/2004 | Broselow |
| D545,429 S | 6/2007 | Hays |
| 8,016,795 B2 | 9/2011 | Barrelle et al. |
| 8,034,033 B2 | 10/2011 | Grinberg |
| 8,062,254 B2 | 11/2011 | Maclean |
| 8,303,547 B2 | 11/2012 | Brown |
| 8,449,499 B2 | 5/2013 | Maclean |
| 8,479,919 B2 | 7/2013 | Kaplan et al. |
| 8,512,296 B2 | 8/2013 | Gabriel et al. |
| 8,747,367 B2 | 6/2014 | Keitel et al. |
| 9,144,648 B2 | 9/2015 | Lesch, Jr. et al. |
| 9,271,896 B2 | 3/2016 | Clements |
| 9,474,864 B2 | 10/2016 | Leary |
| 9,566,388 B1 | 2/2017 | Jones |
| 9,579,259 B2 | 2/2017 | Fernandez |
| 2002/0010429 A1 | 1/2002 | Grogan |
| 2002/0087121 A1 | 7/2002 | Slishman |
| 2003/0176759 A1* | 9/2003 | Hogendijk ........ A61M 25/0105 600/7 |
| 2004/0024368 A1 | 2/2004 | Broselow |
| 2004/0024372 A1 | 2/2004 | Grogan |
| 2007/0093761 A1 | 4/2007 | Veasey et al. |
| 2007/0100288 A1 | 5/2007 | Bozeman et al. |
| 2007/0135772 A1 | 6/2007 | Grogan |
| 2008/0188814 A1* | 8/2008 | Lavi-Loebl ............ A61M 5/28 604/189 |
| 2008/0237177 A1 | 10/2008 | Robinson |
| 2008/0255515 A1* | 10/2008 | Grinberg ............... A61M 5/008 604/111 |
| 2008/0255523 A1* | 10/2008 | Grinberg ............... A61M 5/008 604/192 |
| 2009/0177156 A1* | 7/2009 | MacLean ............ A61M 5/3148 604/135 |
| 2009/0185973 A1 | 7/2009 | Gorny |
| 2009/0264815 A1 | 10/2009 | Grogan |
| 2010/0130961 A1 | 5/2010 | Tucker |
| 2010/0168677 A1* | 7/2010 | Gabriel ............ A61M 5/31551 604/189 |
| 2011/0046560 A1 | 2/2011 | Schiller et al. |
| 2011/0264051 A1* | 10/2011 | Janish ................ A61M 5/31511 604/208 |
| 2011/0313396 A1 | 12/2011 | Chanoch et al. |
| 2011/0313397 A1 | 12/2011 | Gold |
| 2012/0046613 A1 | 2/2012 | Plumptre |
| 2012/0071853 A1 | 3/2012 | Ingram et al. |
| 2012/0165744 A1 | 6/2012 | Jones |
| 2013/0085457 A1 | 4/2013 | Schiff et al. |
| 2013/0204225 A1 | 8/2013 | Creaturo |
| 2013/0226137 A1 | 8/2013 | Brown |
| 2014/0180245 A1 | 6/2014 | Wong et al. |
| 2014/0207079 A1 | 7/2014 | Creaturo |
| 2014/0288506 A1 | 9/2014 | Mumford et al. |
| 2015/0045740 A1 | 2/2015 | Kojima et al. |
| 2015/0073354 A1 | 3/2015 | Creaturo |
| 2015/0196714 A1 | 7/2015 | Creature |
| 2015/0231335 A1 | 8/2015 | Creaturo |
| 2015/0379900 A1 | 12/2015 | Samosky et al. |
| 2016/0022912 A1 | 1/2016 | Hernandez |
| 2016/0022913 A1 | 1/2016 | Creaturo |
| 2016/0045671 A1 | 2/2016 | Creaturo |
| 2017/0000952 A1 | 1/2017 | Leary |
| 2017/0354787 A1* | 12/2017 | Leary ................ A61M 5/31528 |

OTHER PUBLICATIONS

Bindler, et al., "Medication Calculation Ability of Registered Nurses," Journal of Nursing Scholarship, 1991, 23:221-224.

Search Report and Written Opinion for International Patent Application No. PCT/US2015/065544 dated Jun. 30, 2016, 13 pages.

Search Report and Written Opinion for International Patent Application No. PCT/US2017/036543 dated Aug. 21, 2017; 13 pages.

Extended European Search Report for EP Application No. 15870798.4, dated Aug. 6, 2018.

\* cited by examiner

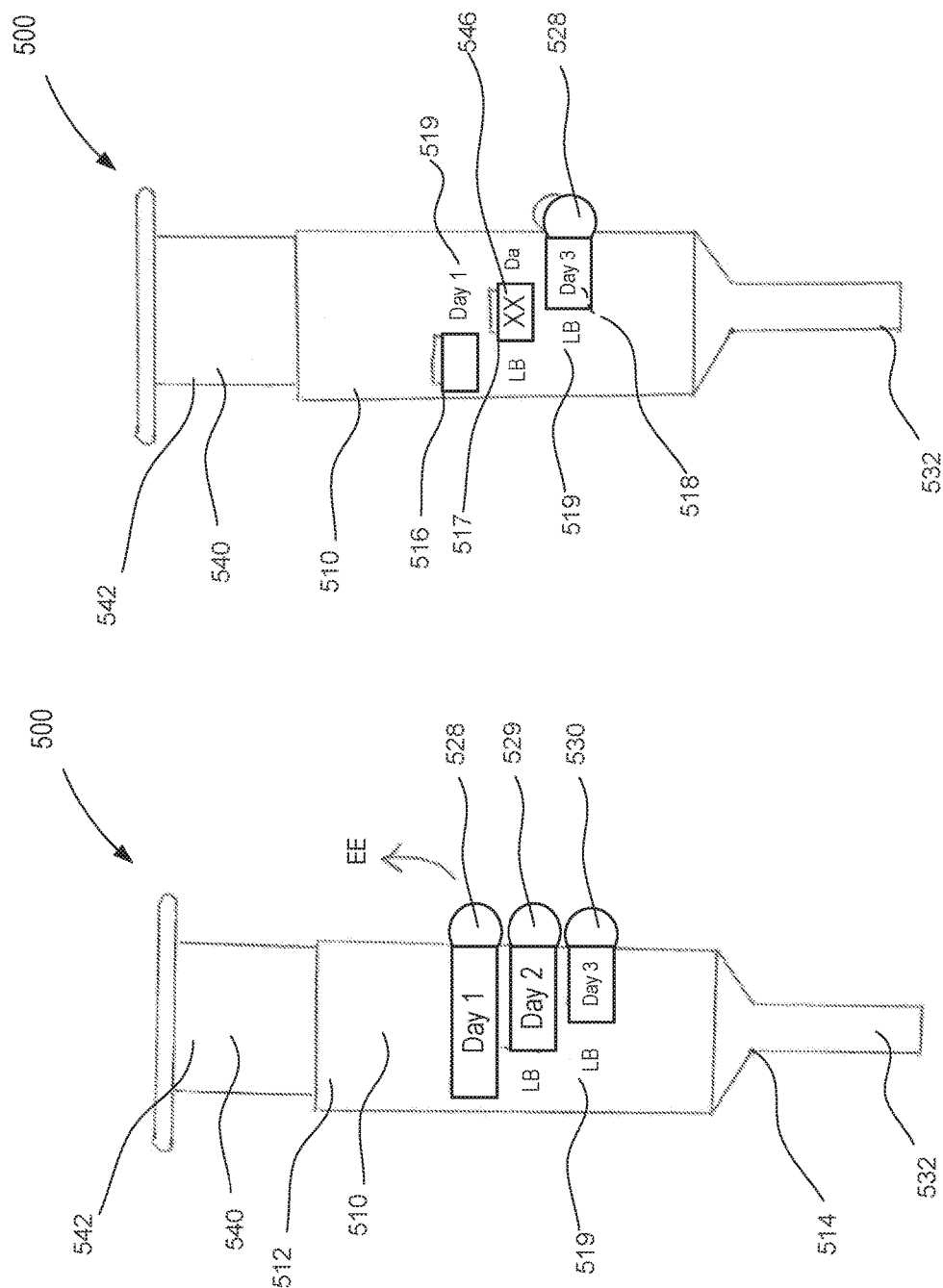

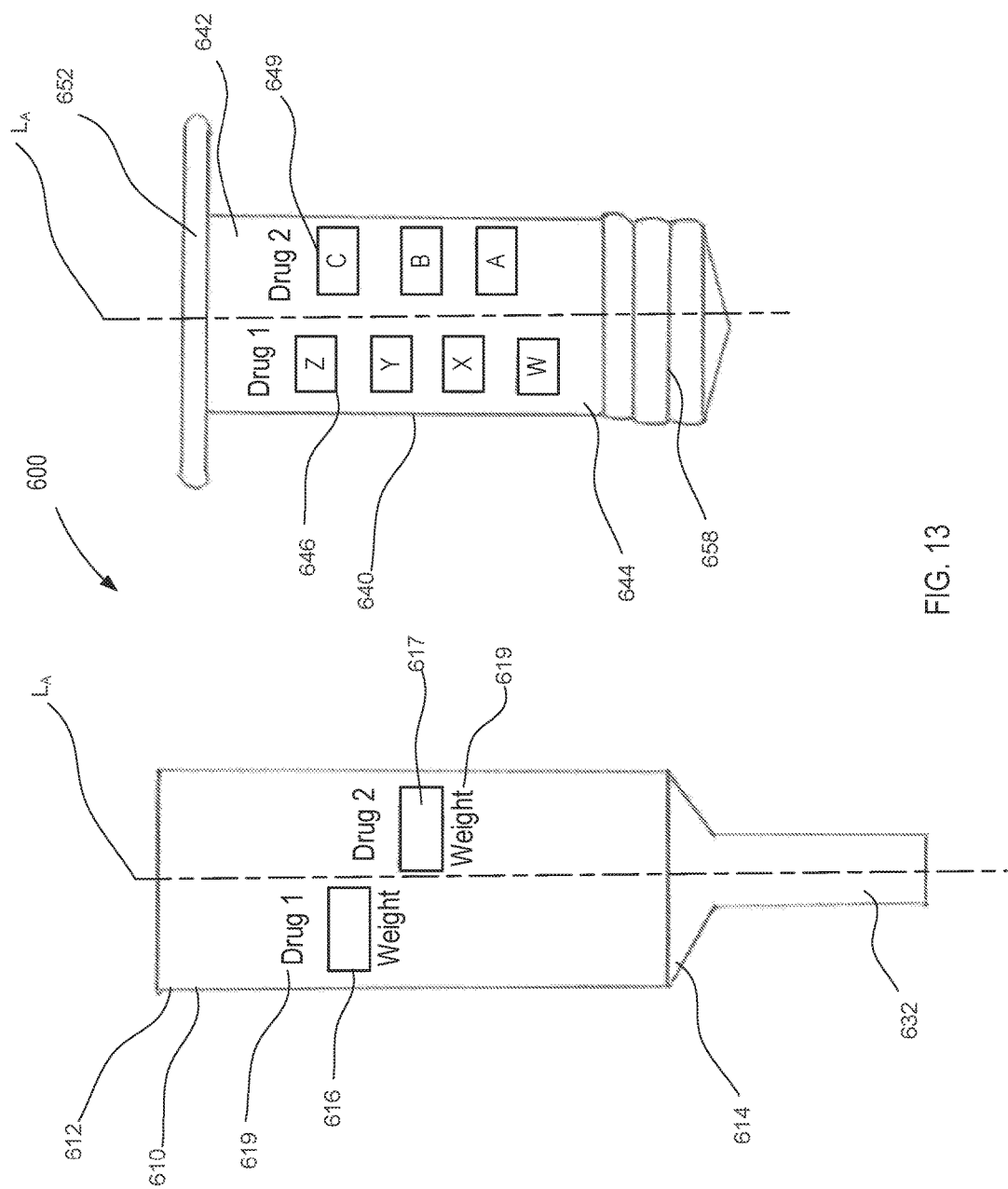

SAFETY SYRINGE AND METHODS FOR ADMINISTRATION OF A MEDICAMENT DOSE BY SUBJECT WEIGHT

CROSS-REFERENCE TO RELATED APPLICATIONS

This application is a divisional of U.S. patent application Ser. No. 14/966,097, entitled "Safety Syringe and Methods for Administration of a Medicament Dose by Subject Weight," filed Dec. 11, 2015, which claims priority to U.S. Provisional Application Ser. No. 62/092,234, entitled "Safety Syringe with Dosage by Weight," filed Dec. 15, 2014, the disclosure of each of which is incorporated herein by reference in its entirety.

BACKGROUND

The embodiments described herein relate to syringes and methods for administering a dose of medicament based on the subject's weight, height, age, or other characteristic.

Some known syringes for delivering dosages of a medicament include a syringe barrel with graduated markings and a plunger that is movable within the barrel to set the dosage and deliver the medicament. The graduated markings for such known syringes are often volumetric (i.e., they indicate the volume of the medicament within the syringe), and thus a user must calculate, convert, or otherwise determine the correct dose based on, among other things, the patient's weight, height and/or age. Additionally, the graduated markings are often very small, are sometimes provided in confusing or unfamiliar units of measure (e.g., teaspoons or milliliters), and require that the user align the plunger along the axis of motion to set the dosage. Moreover, certain medication regimens require that different amounts of the medicament be administered on different days of the treatment. Accordingly, using such known syringes and methods can result in an unacceptable level of medication error and/or "adverse drug events" because of improper dosing (delivering more or less of a drug than the prescribed amount), noncompliance with the regimen (missing a day, administering the improper amount for a given day), or the like.

Although such issues are prevalent with oral delivery of over-the-counter drugs, such as ibuprofen, Tylenol®, cough syrup, or the like, studies have shown that such issues also exist in hospital and clinical settings. For example, one study of adverse drug events at hospitals estimated that although a large number of adverse drug events occurred at the ordering stage, many occurred at the administering stage. Bates, D. W., et al., "Incidence of Adverse Drug Events and Potential Adverse Drug Events," Journal of the American Medical Association, Jul. 5, 1995, Vol. 274, No. 1, pp. 29-30. Another study evaluating the ability of 100 registered nurses to calculate the correct dosage for oral, intramuscular, and intravenous drugs showed an average error rate of about 20 percent or higher, depending on the type of delivery mechanism. Bindler, et al., "Medication Calculation Ability of Registered Nurses," Journal of Nursing Scholarship, 1991, 23:221-224.

One proposed solution to reduce medication error and/or "adverse drug events" is to deliver a predetermined dosage via a single-use prefilled syringe or cartridge. Although convenient for some drugs and/or therapeutic regimens, prefilled syringes are expensive, cumbersome to store, and impractical for many drugs (e.g., over-the-counter painkillers). Moreover, unless a caregiver maintains an inventory of prefilled syringes tailored to a variety of different patients (e.g., weight, age range, or the like), the use of prefilled syringes will still require that the user calculate, convert or otherwise determine the correct dose to be administered.

Other delivery devices for administering dosages, such as insulin pens, include dose-setting mechanisms that include rotatable caps or plungers, bulky multi-part container holders, and the like. Although these devices may be suitable for certain drugs and/or therapeutic regimens, such as chronic care situations (e.g., delivery of insulin), such known devices are impractical for many other drugs and/or therapeutic regimens. For example, administering an over-the-counter cold medicine via an expensive pen injector that requires adherence to specific instructions for use is impractical.

Thus, a need exists for improved methods and devices for easily and accurately delivering medicaments via a syringe.

SUMMARY

Syringes for delivering a dose of medicament are described herein. In some embodiments, an apparatus includes a syringe body and a plunger. The syringe body defines a volume configured to contain a medicament. A proximal end portion of the syringe body includes an engagement portion, and a distal end portion of the syringe body includes a delivery tip. A side wall of the syringe body includes a transparent window. The plunger has a distal end portion configured to move within the volume of the syringe body to convey the medicament. An engagement portion of the plunger is configured to interface with the engagement portion of the syringe body to limit rotation of the plunger about a longitudinal axis of the plunger. An outer surface of the plunger includes a series of indicia, at least one of which is visible through the transparent window.

BRIEF DESCRIPTION OF THE DRAWINGS

FIGS. 11 and 12 are front views of a syringe assembly according to an embodiment, in a first and second configuration, respectively.

FIG. 13 is a front view of the components of a syringe assembly according to an embodiment.

DETAILED DESCRIPTION

Figure 1:
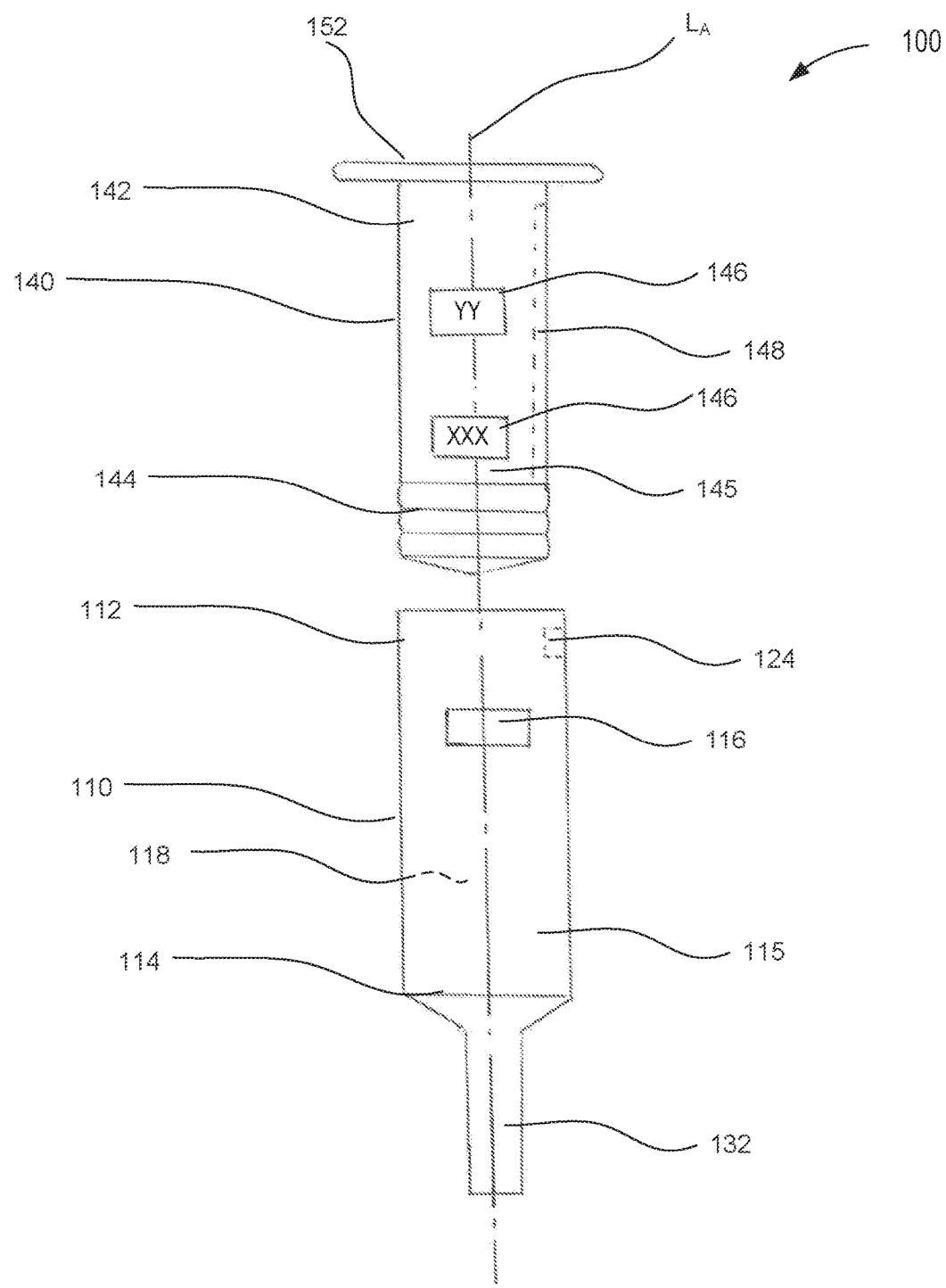
FIG. 1 is an exploded view schematic illustration of a syringe assembly according to an embodiment.

Syringes for easily and accurately delivering a dose of medicament are described herein. In some embodiments, an apparatus includes a syringe body and a plunger. The syringe body defines a volume configured to contain a medicament. A proximal end portion of the syringe body includes an engagement portion, and a distal end portion of the syringe body includes a delivery tip. A side wall of the syringe body includes a transparent window. The plunger has a distal end portion configured to move within the volume of the syringe body to convey the medicament. An engagement portion of the plunger is configured to interface with the engagement portion of the syringe body to limit rotation of the plunger about a longitudinal axis of the plunger. An outer surface of the plunger includes a series of indicia, at least one of which is visible through the transparent window.

In some embodiments, an apparatus includes a syringe body and a plunger. The syringe body defines a volume configured to contain a medicament. The syringe body includes a proximal end flange including an engagement portion. A side wall of the syringe body includes a transparent window. The plunger has a distal end elastomeric member configured to move within the volume of the syringe body to convey the medicament. An engagement portion of the plunger is configured to interface with the engagement portion of the syringe body to limit rotation of the plunger about a longitudinal axis of the plunger. The flange defines an opening through which the elastomeric member can be removed. An outer surface of the plunger includes a series of indicia, at least one of which is visible through the transparent window.

In some embodiments, a plunger can include a series of non-volumetric indicia. The non-volumetric indicia can be associated with a patient's weight, height, age and/or any other suitable dose-setting characteristic. In some embodiments, the series of indicia can be arranged coaxially along a longitudinal axis of the plunger.

In some embodiments, an apparatus includes a syringe body, a set of removable labels and a plunger. The syringe body defines a volume configured to contain a medicament. A side wall of the syringe body includes a set of transparent windows, each of which corresponds to a different dose of a therapeutic regimen. In some embodiments, for example, each window can correspond to a different day of the regimen. A portion of the side wall surrounding each of the transparent windows is opaque. Each of the removable labels is configured to be coupled to the side wall of the syringe body to cover one of the transparent windows. The plunger has a distal end portion configured to move within the volume of the syringe body to convey the medicament. An outer surface of the plunger includes a set of indicia, each of which corresponds to the different dose of the therapeutic regimen. Each indicia is visible through the corresponding transparent window when the corresponding removable label from the set of removable labels is removed from the side wall of the syringe body.

In some embodiments, a kit includes a medicament container and a syringe assembly. The medicament container contains at least one dose of a medicament and defines an opening. The syringe assembly includes a syringe body and a plunger. A proximal end portion of the syringe body includes an engagement portion. A distal end portion of the syringe body includes a delivery tip configured to be disposed within the medicament container to withdraw the dose of the medicament from the container into a volume defined by the syringe body. The syringe body includes a transparent window. A distal end portion of the plunger is configured to move within the volume of the syringe body to convey the medicament. An engagement portion of the plunger is configured to interface with the engagement portion of the syringe body to limit rotation of the plunger about a longitudinal axis of the plunger. An outer surface of the plunger includes a set of dose indicia, at least one of which is visible through the transparent window.

In some embodiments, the kit further includes a lock member removably coupled to the proximal end portion of the syringe body and a proximal end portion of the plunger. The lock member is configured to limit movement of the distal end portion of the plunger within the syringe body. The lock member includes an instruction indicia, such as, for example, drug labeling, warnings, or the like.

In some embodiments, a method includes inserting a delivery tip of a syringe body, which defines a volume therein, into a medicament container. A plunger is moved in a proximal direction within the volume of the syringe body to convey the medicament from the medicament container into the volume. The moving is performed until a dose indicia from a plurality of dose indicia on the plunger is visible through a transparent window defined by the syringe body. The plunger includes an engagement portion configured to interface with an engagement portion of the syringe body to limit rotation of the plunger about a longitudinal axis of the plunger during the moving. The plunger is then moved in a distal direction within the volume of the syringe body to convey the medicament from the volume via the delivery tip.

The term "about" when used in connection with a referenced numeric indication means the referenced numeric indication plus or minus up to 10 percent of that referenced numeric indication. For example, "about 100" means from 90 to 110.

As used in this specification and the appended claims, the words "proximal" and "distal" refer to direction closer to and away from, respectively, an operator of the medical device. Thus, for example, the end of the syringe assembly contacting the patient's body (e.g., being inserted into the mouth, supporting a needle, or the like) would be the distal end of the syringe assembly, while the end opposite the distal end would be the proximal end of the syringe assembly.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

The term "fluid-tight" is understood to encompass hermetic sealing (i.e., a seal that is gas-impervious) as well as a seal that is only liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at pressures of less than about 5 psig, less than about 10 psig, less than about 20 psig, less than about 30 psig, less than about 50 psig, less than about 75 psig, less than about 100 psig, and all values in between. Any residual fluid layer that may be present on a portion of a wall of a container after component defining a "substantially-fluid tight" seal are moved past the portion of the wall are not considered as leakage.

The term "opaque" is understood to include structures (such as portions of a syringe body) that are not transparent and/or that do not permit an object to be clearly or distinctly seen through the structure. The term "opaque" or "substantially opaque" or "semi-opaque" when used in connection with the description of a side wall of a syringe body or any other structure described herein is intended to convey that objects cannot be clearly seen through the side wall. A side wall (or portion thereof) described as being "opaque" or "substantially opaque" or "semi-opaque" is understood to include structures that may have a blocking color, or that may not have a color, but that are otherwise hazy, blurry, smeared, textured or the like.

Figure 4:
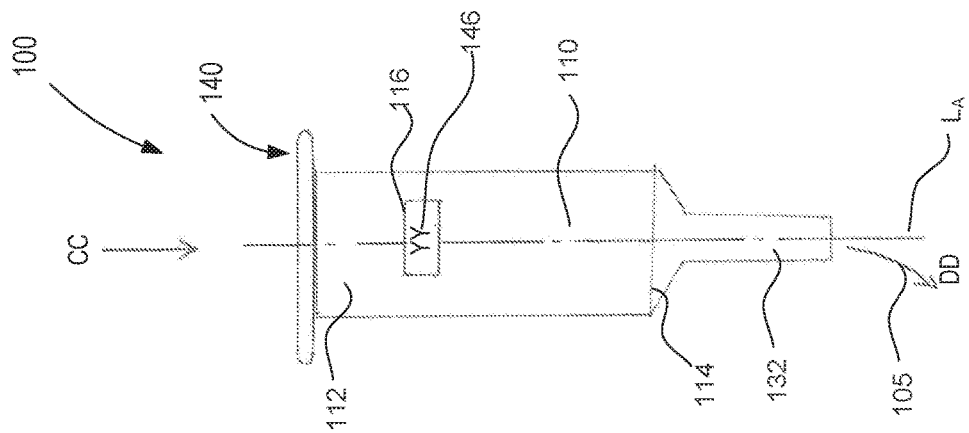
FIGS. 2-4 are schematic illustrations of the syringe assembly shown in FIG. 1, in a first, second, and third configuration, respectively.
Figure 3:
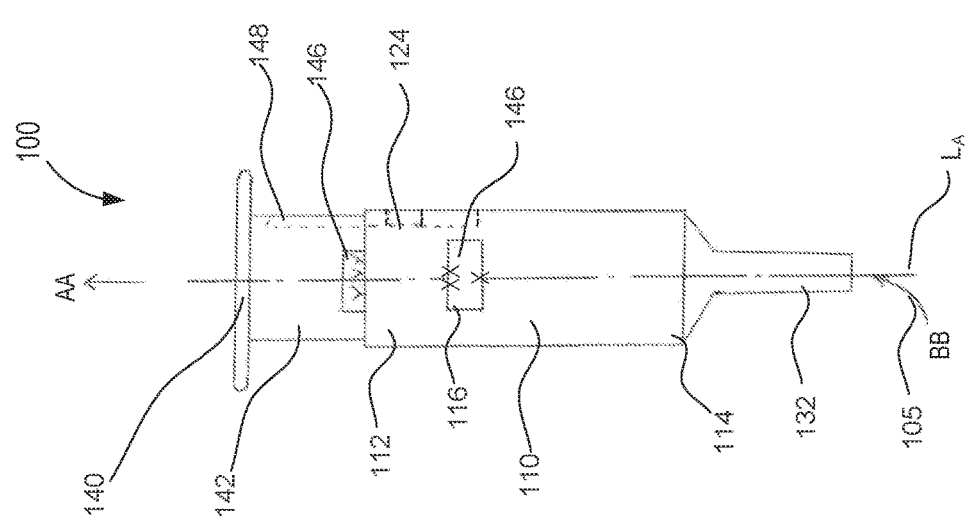
Figure 2:
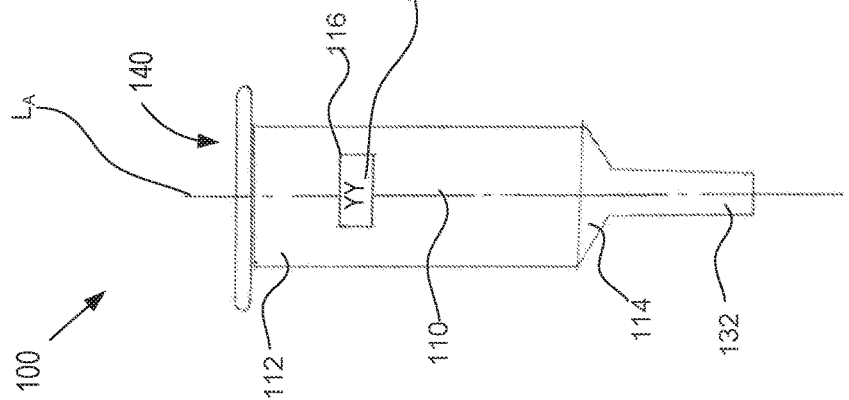

FIGS. 1-4 are schematic illustrations of a syringe assembly 100 according to an embodiment that includes a syringe body 110 and a plunger 140. FIG. 1 shows an exploded view of the syringe assembly 100 to illustrate the syringe body 110 and the plunger 140. FIGS. 2-4 show the syringe assembly 100 in a first, second, and third configuration, respectively. The syringe body 110 includes a side wall 115, and defines an interior volume 118 within which a medicament can be contained. The syringe body 110 includes a proximal end portion 112 having an engagement portion 124, and defines a longitudinal axis $L_A$. The engagement portion 124 can be any suitable structure or mechanism to engage and/or interface with a corresponding engagement portion of the plunger 140 to limit rotation of the plunger 140 within the syringe body 110 about the longitudinal axis $L_A$. For example, in some embodiments, the engagement portion 124 can include a protrusion configured to be disposed within a corresponding groove of the plunger 140. In other embodiments, the engagement portion 124 can include a recessed portion configured to receive a protrusion of the plunger 140. In yet other embodiments, the engagement portion 124 can include a splined surface that interfaces with a corresponding splined surface of the plunger 140 to limit, reduce and/or prevent rotation of the plunger 140 within the syringe body 110.

The syringe body 110 includes a distal end portion 114 having a delivery tip 132. The delivery tip 132 can be any suitable tip or member through which the medicament can be conveyed either into or out of the volume 118 of the syringe body 110. In some embodiments, the delivery tip 132 can be a protrusion extending from the syringe body 110 that can be received within a medicament container (e.g., bottle, vial or the like) and that can also deliver the medicament orally to the patient. In other embodiments, the delivery tip 132 can a tapered fitting (such as a Luer fitting) that is adapted to couple the distal end portion 114 of the syringe body 110 to a needle (not shown).

The syringe body 110 includes a transparent window 116. As described in more detail below, the transparent window 116 is positioned such that at least one indicia 146 on the plunger 140 is visible therethrough. The transparent window 116 can be of any suitable size and/or shape to allow visual access to the indicia 146. Thus, although the transparent window 116 is shown as being rectangular, in other embodiments, the transparent window 116 (and any of the transparent windows shown and described herein) can be any shape, such circular, triangular, elliptical or the like. In some embodiments, the transparent window is sized such that only one indicia from the set of indicia 146 is visible through the transparent window 116 at a time. In some embodiments, a portion of the side wall 115 surrounding the transparent window 116 is opaque (or semi-opaque), thereby "framing" or accentuating the window 116. In this manner, during use, the indicia displayed within the transparent window 116 are clearly accentuated to the user. In some embodiments, for example, the side wall 115 of the syringe body 110 can include markings (e.g., thick lines, colors or the like) to highlight the transparent window 116.

In some embodiments, the syringe body 110 (or any of the syringe bodies shown and described herein) includes an opaque or semi-opaque label (not shown in FIGS. 1-4) that is coupled to at least a portion of the syringe body 110. The opaque label can define an opening that is aligned with and/or that defines the transparent window 116 of the syringe body 110. In such embodiments, the opaque label can include markings to highlight and/or "frame" the transparent window 116. Moreover, the opaque label can include instructions or other indicia associated with the medicament, therapeutic regimen or the like. For example, in some embodiments, an opaque label can include markings such as "weight," "day 1," and/or the drug name.

In some embodiments, the syringe body the syringe body can be constructed from a clear material (e.g., plastic or glass), and the syringe body 110 can include an opaque label that defines the transparent window 116. In other embodiments, the syringe body can include a monolithically constructed opaque or semi-opaque portion. Such portions can include a light blocking color, or can be devoid of color, but can otherwise by hazy, blurred or textured to prevent medicament inside of the syringe body from being clearly seen.

The plunger 140 includes a proximal end portion 142 and a distal end portion 144 and defines a longitudinal axis $L_A$. The distal end portion 144 is configured to move within the interior volume 118 the syringe body 110 to convey a medicament 105. More particularly, as described in more detail below, the distal end portion 144 can reciprocate within the syringe body 110 along the longitudinal axis $L_A$ to convey the medicament 105 into the volume 118 (as shown by the arrow BB in FIG. 3), and convey the medicament 105 out of the volume 118 (as shown by the arrow DD in FIG. 4). In some embodiments, the distal end portion 144 includes an elastomeric member defining a fluid-tight (or substantially fluid-tight) seal with the side wall 115 of the syringe body 110.

The plunger 140 includes an engagement portion 148 configured to interface with the engagement portion 124 of the syringe body 110 to limit rotation of the plunger 140 about its longitudinal axis $L_A$. The engagement portion 148 can be any suitable structure or mechanism to engage and/or interface with the engagement portion 124 of the syringe body 110 to limit rotation of the plunger 140 within the syringe body 110 about the longitudinal axis $L_A$. For example, in some embodiments, the engagement portion 148 can include a protrusion configured to be disposed within a corresponding groove of the syringe body 110. In other embodiments, the engagement portion 148 can include a recessed portion configured to receive a protrusion of the syringe body 110. In yet other embodiments, the engagement portion 148 can include a splined surface that interfaces with a corresponding splined surface of the syringe body 110 to limit, reduce and/or prevent rotation of the plunger 140 within the syringe body 110

The plunger 140 includes an outer surface 145 having a series of indicia 146. As shown in FIGS. 3 and 4, at least one of the indicia from the series of indicia 146 is visible through the transparent window 116 of the syringe body 110. In this manner, the indicia 146 can provide a visual indication of the dosage of medicament 105 drawn into the syringe body 110. More specifically, because the indicia 146 are in a fixed position on the plunger 140 and the transparent window 116 is in a fixed position on the syringe body 110, the position of the plunger 140 within the syringe body 110 at which one of the indicia 146 is visible via the transparent window 116 corresponds to a particular volume (i.e., dosage volume) within the syringe body 110. In some embodiments, however, the indicia 146 can be non-volumetric indicia that correspond to a characteristic of the patient. For example, in some embodiments, the indicia 146 can correspond to a weight, height, age, target body weight, and/or body mass index (BMI) of the patient. In other embodiments, the indicia 146 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

In some embodiments, the series of indicia 146 can include both a series of dosage amounts (e.g., a series of weight ranges corresponding the desired dosage) and one or more instructions. For example, in some embodiments, one indicia from the series of indicia 146 can be configured and/or position to be visible via (or appear within) the transparent window 116 when the syringe assembly 100 is in a "ready" (or empty) state. This is shown, for example, in FIG. 2 (the syringe assembly 100 in the first configuration), which shows the indicia YY as being visible via the transparent window 116 when the plunger 140 is in the distal-most position within the syringe body 110. In some embodiments, an instruction indicia 146 can include an identification of the drug with which the syringe assembly 100 should be used. In this manner, the instruction indicia 146 can minimize the likelihood that the syringe assembly 100 will be used with an improper medicament.

The series of indicia 146 can be arranged along the outer surface 145 in any suitable manner or orientation. For example, in some embodiments, the series of indicia 146 is arranged coaxially along the longitudinal axis $L_A$. In this manner, when the plunger 140 is reciprocated along the longitudinal axis $L_A$ within the internal volume 118 of the syringe body 110, each of the indicia 146 will be visible through the transparent window 116 at given plunger position.

In use, the distal end portion 144 of the plunger 140 can be reciprocated within the syringe body 110 along the longitudinal axis $A_L$ to convey a medicament 105 into and/or out of the internal volume 118 of the syringe body 110. FIG. 2 shows the syringe assembly 100 in its initial or "ready" configuration. In the initial configuration, the plunger 140 is positioned at its distal-most position within the syringe body 110. In the initial configuration, a first indicia 146 (the indicia "YY") is shown as being visible through the transparent window 146. The first indicia 146 (indicated as "YY") can be, for example, an instruction indicia, a warning, a drug label, or the like. Although the first indicia 146 (the indicia "YY") is shown as being visible through the transparent window 146 when the syringe assembly 100 is in its initial configuration, in other embodiments, no indicia is viewable through the transparent window 116 when the syringe assembly 100 is in its first configuration.

To prepare a dose of the medicament 105 for delivery, the delivery tip 132 is placed in fluid communication with a source of medicament (e.g., a medicament container, not shown in FIGS. 1-4), and the plunger 140 is moved proximally, as shown by the arrow AA in FIG. 3. The movement of the distal end portion 144 of the plunger 140 within the syringe body 110 increases the internal volume 118, which, in turn, produces a vacuum that draws the medicament 105 into the syringe body 110 as shown by the arrow BB in FIG. 3. As shown in FIG. 3, the plunger 140 is moved proximally until a second indicia 146 (the indicia "XXX") is visible through a transparent window 116. In this manner, the syringe assembly 100 is placed in its second (or "dosage set") configuration. The second indicia 146 (indicated as "XXX") can be, for example, a dose indicia. In some embodiments, the second indicia 146 can be a non-volumetric indicia (e.g., a weight range, a height range and/or an age range of the patient). In this manner, the user can easily set the desired dosage by withdrawing the plunger 140 until the second indicia 146 (the indicia "XXX") is visible within the transparent window 116. This arrangement allows the dosage to be set without the need for calculation, conversion or consideration of the patient's characteristics to a volumetric measurement.

In some embodiments, the side wall 115 of the syringe body 110 includes a syringe detent (not shown in FIGS. 1-4) configured to engage one or more plunger detents (not shown in FIGS. 1-4) to resist movement of the distal end portion 144 of the plunger 140 within the syringe body 110 when each of the series of indicia 146 is visible through the transparent window. In this manner, the user can receive a tactile sensation (e.g., a slight snap, click or vibration) when each of the indicia 146 are aligned with and/or visible via the transparent window 116. In this manner, the syringe assembly 100 can allow for a series of discrete intervals of plunger movement within the syringe body 110.

As described above, during the movement of the plunger 140, the engagement portion 148 of the plunger 140 interfaces with the engagement portion 124 of the syringe body 110 to limit rotation of the plunger 140 about a longitudinal axis $L_A$ of the plunger. In this manner, the indicia 146 remain radially aligned with the transparent window 116, thus ensuring that the indicia 146 will be visible through the transparent window 116 when the plunger 140 is in the corresponding longitudinal position within the syringe body 110.

Although shown as having only two indicia 146, in other embodiments, the outer surface 145 of the plunger 140 can include any number of indicia 146. For example, in some embodiments, the plunger 140 can include a series of indicia 146 corresponding to the following weight ranges of the patient: 12 to 17 pounds, 18 to 23 pounds, 24 to 35 pounds, 36 to 47 pounds, 48 to 60 pounds, 61 to 75 pounds, 76 to 90 pounds, and greater than 90 pounds. In other embodiments, the plunger 140 can include a series of indicia 146 corresponding to the following age ranges of the patient: 6 to 18 months, 18 months to 3 years, 3 to 5 years, 6 to 11 years, and 12 years and higher. In yet other embodiments, the plunger 140 can include a series of indicia 146 that do not correspond to ranges (e.g., they may correspond to a specific weight, age, height, lab test result or the like). Such indicia may include for example, a metric/English marking (10 lb/4.5 kg).

Although shown as having a series of indicia 146 arranged longitudinally along the plunger 140, in other embodiments, the plunger can also include an indicia (e.g., an instruction indicia, a warning or the like) on the proximal end portion that is exposed from the syringe body 110 when the syringe assembly 100 is in its first configuration. For example, in some embodiments, the plunger 140 can include an indicia (not shown in FIGS. 1-4) facing outwardly from the activation surface 152 or "handle" of the plunger 140.

To deliver the dosage withdrawn, the user then places the delivery tip 132 in the desired location (e.g., in the patient's mouth) and moves the plunger 140 distally, as shown by the arrow CC in FIG. 4. The movement of the distal end portion 144 of the plunger 140 within the syringe body 110 decreases the internal volume 118, which, in turn, produces a pressure that conveys the medicament 105 out of the syringe body 110 as shown by the arrow DD in FIG. 4. This movement places the syringe assembly 100 in its third (or dose delivered) configuration.

In some embodiments, the syringe assembly 100 can be cleaned for reuse by repeatedly reciprocating the plunger 140 within the syringe body 110 to rinse with water, saline solution or the like. In other embodiments, the syringe assembly 100 can be disassembled for cleaning (e.g., by decoupling the engagement portion 148 of the plunger 140 from the engagement portion 124 of the syringe body 110.

The syringe body 110 and any of the syringe bodies shown and described herein can be constructed of any suitable material, such as hard plastic or glass. In some embodiments, the syringe body 110, or any of the syringe bodies described herein, can be constructed from moldable plastic materials such as, for example, a polymeric plastic including, but not limited to, polyethylene, polypropylene, polycarbonate, polytetrafluoroethylene (PTFE), a phenol formaldehyde resin (e.g., Bakelite) and/or the like. In some embodiments, the syringe body 110, or any of the syringe bodies shown and described herein, is monolithically constructed. For example, the syringe body 110 and any of the syringe bodies shown and described herein can be molded to form a single component having a constant cross-sectional diameter. In other embodiments, however, the syringe body 110, and any of the syringe bodies shown and described herein, can be constructed from multiple separate components that are later joined together.

The plunger 140 and any of the plungers shown and described herein can be constructed of any suitable material, such as hard plastic. In some embodiments, the plunger 140, or any of the plungers described herein, can be constructed from moldable plastic materials such as, for example, a polymeric plastic including, but not limited to, polyethylene, polypropylene, polycarbonate, polytetrafluoroethylene (PTFE), a phenol formaldehyde resin (e.g., Bakelite) and/or the like. In some embodiments, the plunger 140, or any of the plungers shown and described herein, is monolithically constructed. In other embodiments, however, the plunger 140, and any of the plungers shown and described herein, can be constructed from multiple separate components that are later joined together. For example, in some embodiments, the plunger 140 can include a hard plastic member and an elastomeric member (not identified in FIGS. 1-4) that seals the medicament 105 within the volume 118. In such embodiments, the elastomeric member can be of any design or formulation suitable for contact with the medicament 105.

Figure 5:
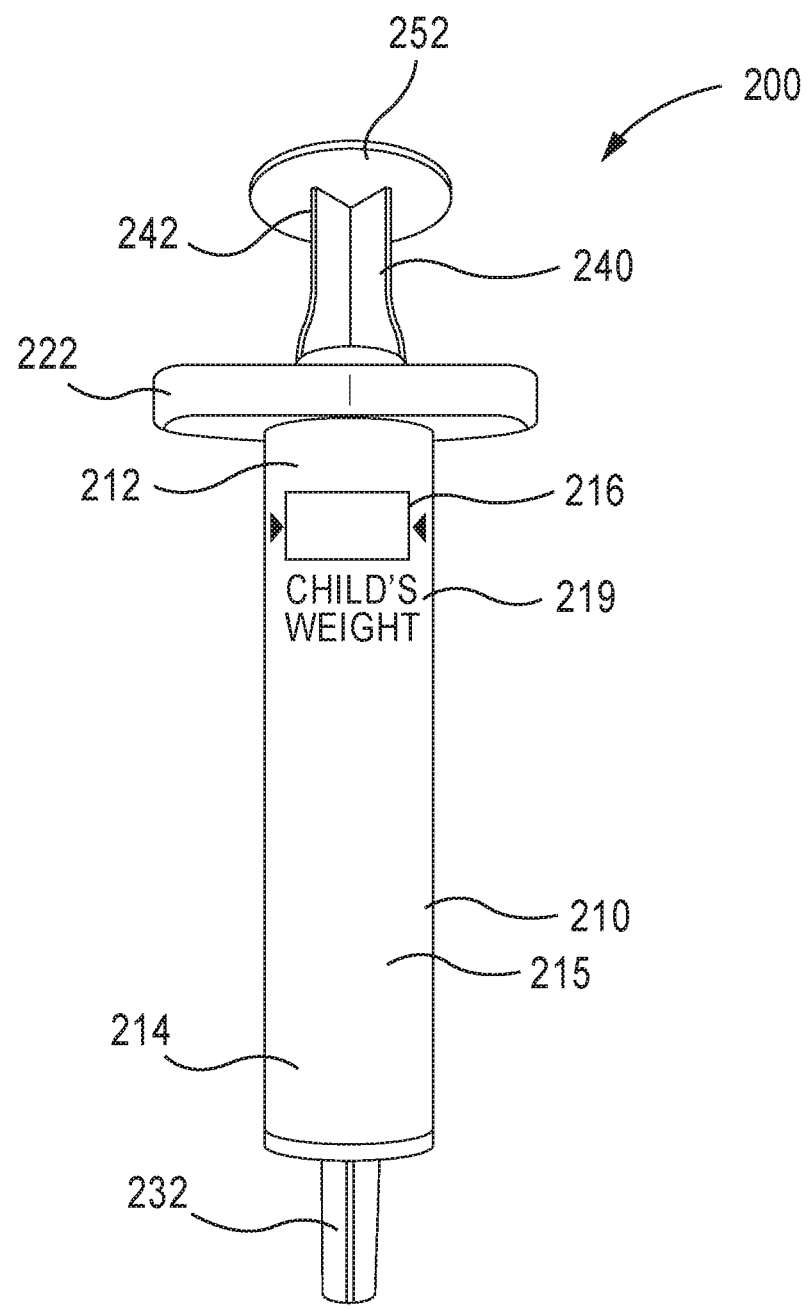
FIG. 5 is a front perspective view of a syringe assembly according to an embodiment.
Figure 6:
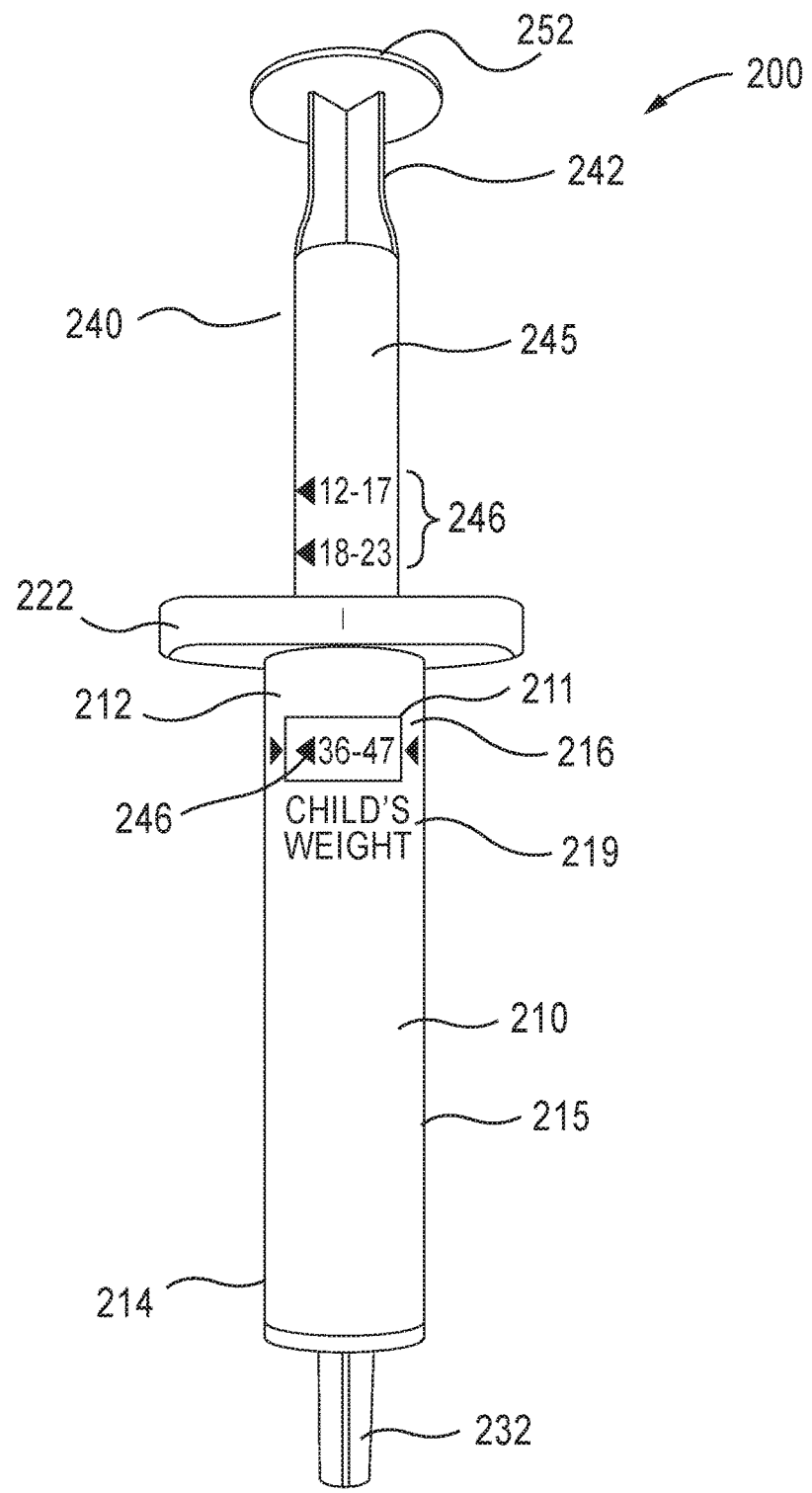
FIGS. 6 and 7 are a front view and a side perspective view, respectively, of the syringe assembly shown in FIG. 5.
Figure 7:
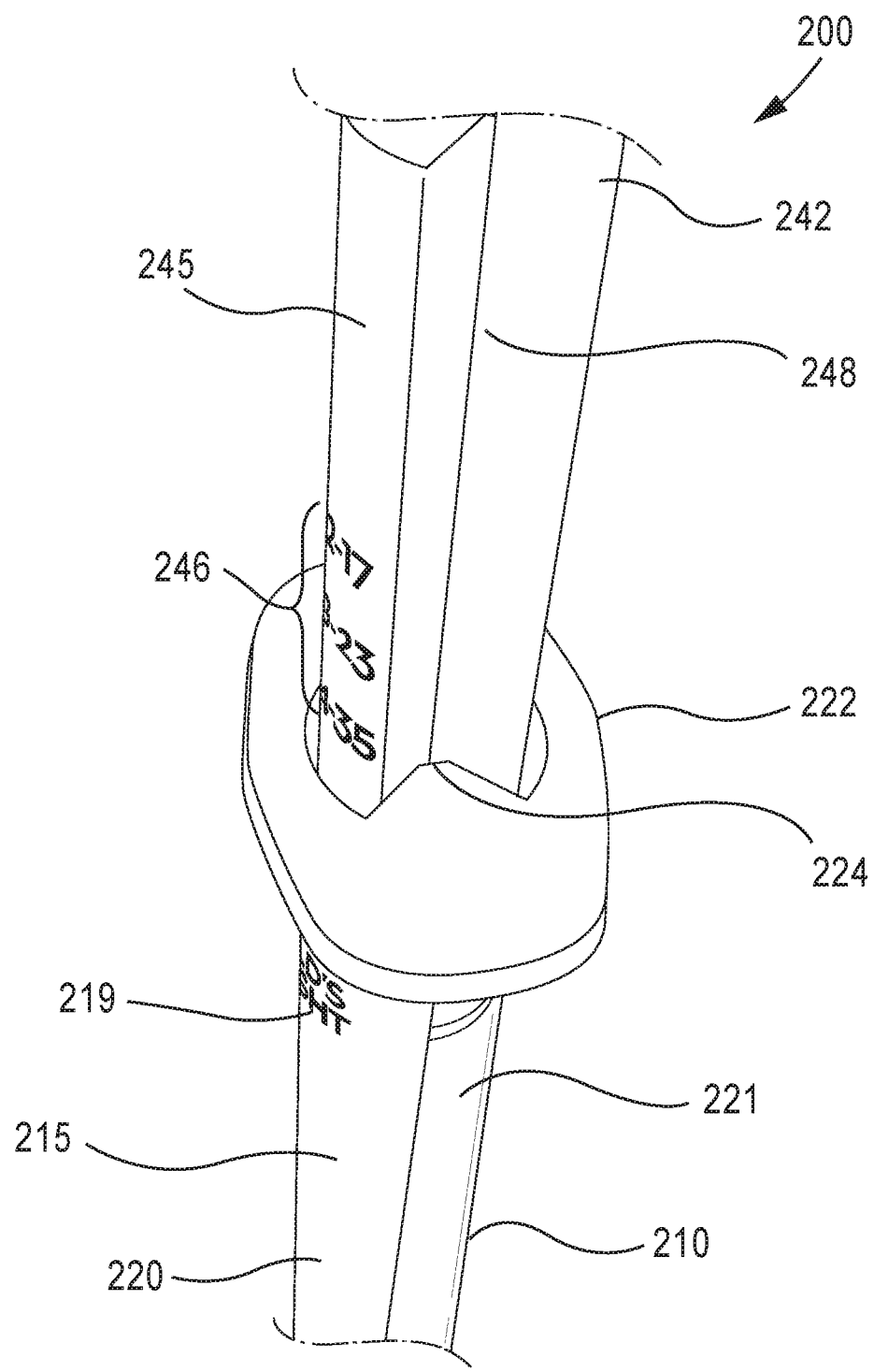

In some embodiments, a syringe body can include a flange (either monolithically formed along with the remainder of the syringe body or formed separately and later coupled to the remainder of the syringe body). For example, FIGS. 5-7 show a syringe assembly 200 according to an embodiment that includes a syringe body 210 and a plunger 240. The syringe body 210 includes a side wall 215, and defines an interior volume within which a medicament can be contained. The syringe body 210 includes a proximal end portion 212 and a distal end portion 214, and defines a longitudinal axis (not identified in FIGS. 5-7). The distal end portion 214 has a delivery tip 232. The delivery tip 232 can be any suitable tip or member through which the medicament can be conveyed either into or out of the syringe body 210.

The proximal end portion 212 includes a flange 222 that can be manipulated by a user to move the plunger 240 within the syringe body 210. As shown in FIG. 7, the flange 222 includes an engagement protrusion 224 that is disposed within and/or interfaces with a corresponding engagement groove 248 of the plunger 240 to limit rotation of the plunger 240 within the syringe body 210 about the longitudinal axis. In this manner, as discussed below, the series of indicia 246 on the plunger 240 remain in a constant radial position relative to the syringe body 210 during use.

As shown in FIG. 7, the syringe body 210 includes an opaque (or semi-opaque) portion 220 and a transparent portion 221. The transparent portion 221 can extend the length of the syringe body 210, and can allow a user to visually inspect the medicament withdrawn into the syringe body 210. For example, by visually inspecting the medicament via the transparent portion 221, a user can verify that the medicament was fully withdrawn into the syringe body 210 (as opposed to withdrawing a significant amount of air), can evaluate the status of the medicament or the like. Moreover, in some embodiments, the transparent portion 221 can include graduated markings to allow the user to verify the volume of medicament conveyed into the syringe.

The syringe body further includes a transparent window 216 within the opaque portion 220. As described in more detail below, the transparent window 216 is positioned such that at least one indicia 246 on the plunger 240 is visible via the transparent window 216. The transparent window 216 can be of any suitable size and/or shape to allow visual access to the indicia 246. Thus, although the transparent window 216 is shown as being rectangular, in other embodiments, the transparent window 216 (and any of the transparent windows shown and described herein) can be any shape, such circular, triangular, elliptical or the like. As shown in FIG. 6, the transparent window is sized such that only one indicia from the set of indicia 246 is visible through the transparent window 216 at a time.

The opaque portion 220 of the syringe body 210 includes a visible frame 211 that surrounds the transparent window 216. In this manner, during use, the indicia displayed within the transparent window 216 are clearly accentuated to the user. Although shown as being a solid rectangular box that completely surrounds the transparent window 216, in other embodiments, the visible frame 211 can be any pattern, and can only partially surround the transparent window. The opaque portion 220 of the syringe body 210 includes instruction indicia 219. More specifically, the instruction indicia 219 include the characteristic of the patient to be considered when setting the dosage (e.g., "child's weight"), and can also include alignment marks or arrows. In other embodiments, the indicia 219 can include markings such as the identification of the regimen (e.g., "day 2") and/or the drug name.

The plunger 240 includes a proximal end portion 242 and a distal end portion (not identified in FIGS. 5-7) that moves within the interior volume 218 the syringe body 210 to convey a medicament. More particularly, as described in more detail below, the distal end portion can reciprocate within the syringe body 210 along the longitudinal axis to convey the medicament into the syringe body 210 (to set a dosage), and convey the medicament out of the syringe body 210 (to deliver the dosage). The proximal end portion 242 of the plunger 240 includes an actuation flange 252 that can be grasped and/or manipulated by a user to move the plunger 240 within the syringe body 210.

The plunger 240 includes an outer surface 245 having a series of indicia 246. As shown in FIG. 6, at least one of the indicia from the series of indicia 246 is visible through the transparent window 216 of the syringe body 210. In this manner, the indicia 246 can provide a visual indication of the dosage of medicament drawn into the syringe body 210. More specifically, because the indicia 246 are in a fixed position on the plunger 240 and the transparent window 216 is in a fixed position on the syringe body 210, the position of the plunger 240 within the syringe body 210 at which one of the indicia 246 is visible via the transparent window 216 corresponds to a particular volume (i.e., dosage volume) within the syringe body 210. As shown, the indicia 246 are non-volumetric indicia that correspond to the patient's weight. For example, in some embodiments, the indicia 246 can correspond to a weight, height, age, target body weight, and/or body mass index (BMI) of the patient. In other embodiments, the indicia 246 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

As shown in FIG. 7, the plunger 240 includes an engagement groove 248 configured to interface with the engagement protrusion 224 of the syringe body 210 to limit rotation of the plunger 240 about its longitudinal axis $L_A$. The engagement groove 248 can be any suitable shape (e.g., rectangular, dovetail, or the like) to engage and/or interface with the engagement protrusion 224 of the syringe body 210 to limit rotation of the plunger 240 within the syringe body 210 about the longitudinal axis $L_A$. In this manner, the indicia 246 remain radially aligned with the transparent window 216, thus ensuring that the indicia 246 will be visible through the transparent window 216 when the plunger 240 is in the corresponding longitudinal position within the syringe body 210.

Although shown as including indicia 246 corresponding to specific weight ranges, in other embodiments, the outer surface 245 of the plunger 240 can include any number of indicia 246 covering any number of different characteristics and/or ranges. For example, in some embodiments, the plunger 240 can include a series of indicia 246 corresponding to the following age ranges of the patient: 6 to 28 months, 28 months to 3 years, 3 to 5 years, 6 to 11 years, and 12 years and higher. In other embodiments, the indicia 246 or any of the indicia described herein can be associated with any characteristic, range and/or values described herein. Although shown as having a series of indicia 246 arranged longitudinally along the plunger 240, in other embodiments, the plunger can also include an indicia (e.g., an instruction indicia, a warning or the like) on the actuation surface 252 of the syringe body 210.

Figure 9:
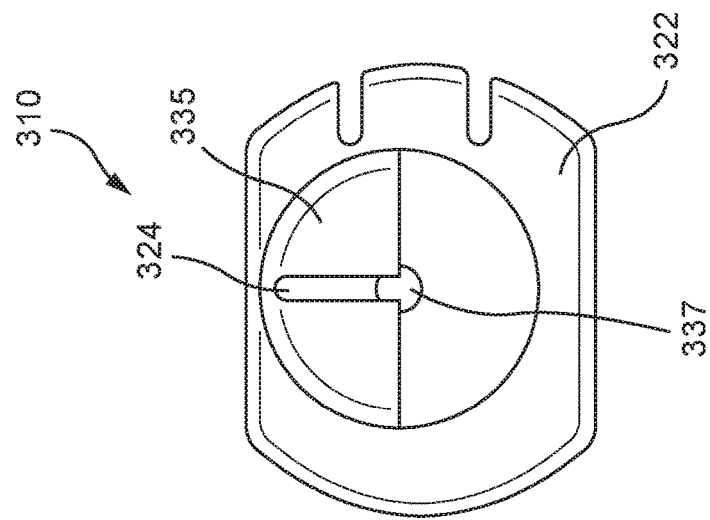
FIGS. 8 and 9 are a side view and a top view, respectively, of a portion of a syringe assembly according to an embodiment.
Figure 8:
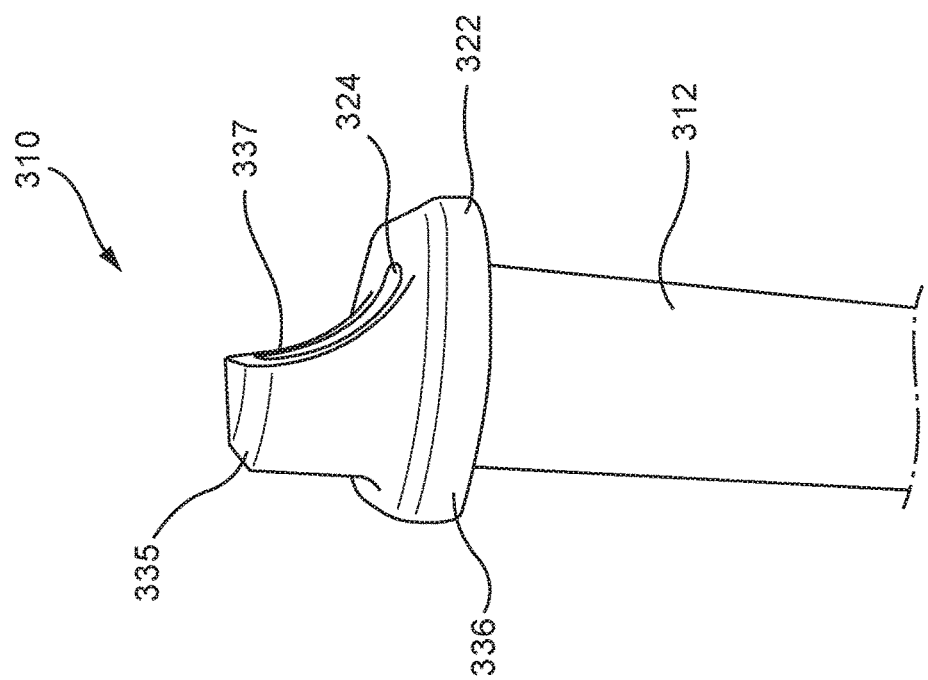

Although some of the syringe bodies are shown and described herein as being monolithically constructed, in other embodiments, a syringe body can include body portion that defines a medicament volume and a flange that is separately constructed and affixed to the body portion. For example, FIGS. 8 and 9 show a portion of a syringe body 310 having a proximal end portion 312 that includes a flange 322. The flange 322 is separately constructed and coupled to the syringe body 310, and can be included in any of the syringe bodies described herein. As shown, the flange 322 includes a proximal end portion 335 and a distal end portion 336. The distal end portion 336 is coupled to the proximal end portion 312 of the syringe body 310. The distal end portion 336 can be coupled to the syringe body 310 via any suitable mechanism, such as, for example, by an interference (or "snap") fit, a threaded connection, an adhesive joint, a weld, or the like.

The proximal end portion 335 of the flange 322 defines an engagement slot or groove 324 that receives and/or interfaces with a corresponding engagement protrusion of a plunger (not shown in FIGS. 8 and 9) to limit rotation of the plunger within the syringe body 310. In this manner, as discussed herein, any indicia or markings on the plunger can remain in a constant radial position relative to the syringe body 310 during use. This arrangement ensures that the indicia will be visible through the transparent window (not shown in FIGS. 8 and 9) of syringe body 310.

The proximal end portion 335 of the flange 322 also defines a lateral opening 337. The lateral opening 337 has a size and shape such that the distal end portion of the plunger (not shown) can be removed from the syringe body 310 via the lateral opening 337. Similarly stated, the lateral opening 337 is configured to allow the distal end portion of the plunger (including any elastomeric member coupled thereto) to pass therethrough. This arrangement allows for assembly and/or disassembly of the syringe assembly after the flange 322 is coupled to the syringe body 310.

Although the syringe body 110 and the syringe body 210 are each shown as including a single transparent window (the transparent windows 116 and 216, respectively), in other embodiments, a syringe body 110 can include any number of transparent windows through which any number of different plunger indicia can be viewed. For example, in some embodiments, a syringe body can include two transparent windows that are spaced apart from each other. Similarly stated, in some embodiments, a syringe body can include two transparent windows that are non-contiguous (e.g., the two transparent windows can be separated by an opaque portion or label). In such embodiments, a first plunger indicia can be visible through the first transparent window when the plunger is in a first position within the syringe body, and a second plunger indicia can be visible through the second transparent window when the plunger is in a second position within the syringe body.

Figure 10:
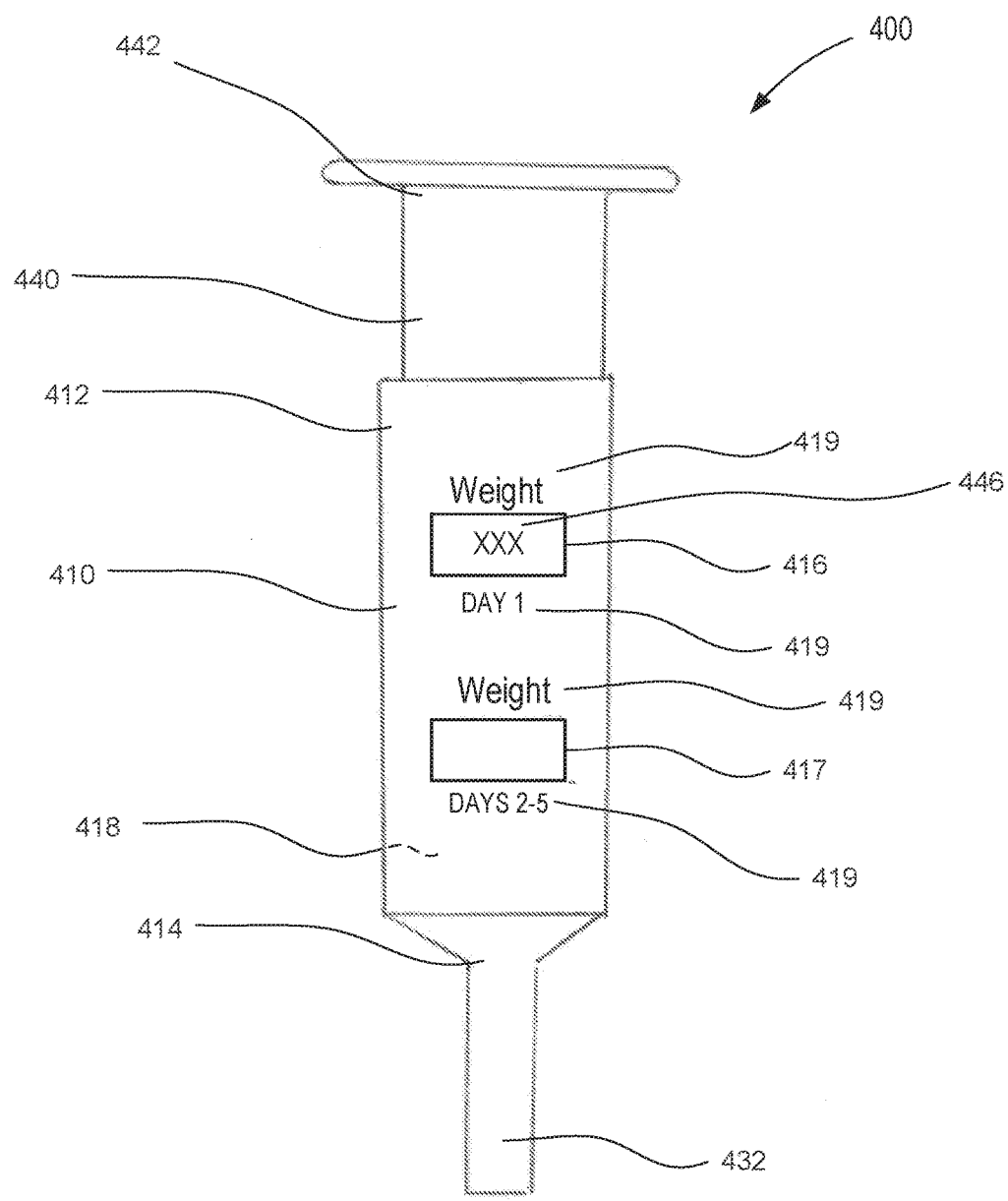
FIG. 10 is a front view of a syringe assembly according to an embodiment.

As one example of a syringe assembly having multiple transparent windows, FIG. 10 shows a syringe assembly 400 that includes a plunger 440 and a syringe body 410 having two transparent windows. The syringe body 410 includes a side wall, and defines an interior volume 418 within which a medicament can be contained. The syringe body 410 includes a proximal end portion 412 and a distal end portion 414. The distal end portion 414 includes a delivery tip 432, which can be any suitable tip or member through which the medicament can be conveyed either into or out of the syringe body 410. In some embodiments, the delivery tip 432 can be a protrusion extending from the syringe body 410 that can be received within a medicament container (e.g., bottle, vial or the like) and that can also deliver the medicament orally to the patient. In other embodiments, the delivery tip 432 can a tapered fitting (such as a Luer fitting) that is adapted to couple the distal end portion 414 of the syringe body 410 to a needle (not shown).

The syringe body 410 includes a first transparent window 416 and a second transparent window 417. The first transparent window 416 and the second transparent window 417 are each positioned such that at least one indicia 446 on the plunger 440 is visible therethrough when the plunger 440 is in a particular longitudinal position within the syringe body 410 (i.e., at a position that corresponds to a dosage). As shown, the outer surface of the syringe body 410 also includes a series of instruction indicia 419. The instruction indicia 419 are specific to and/or unique to each of the first transparent window 416 and the second transparent window 417. More specifically, the first transparent window 416 is adjacent to, framed by and/or associated with the instruction indicia 419 indicating "DAY 1" and "Weight" and the second transparent window 417 is adjacent to, framed by and/or associated with the instruction indicia 419 indicating "DAYS 2-5" and "Weight." As described in more detail below, this arrangement allows the syringe assembly 400 to easily identify the dosage of a drug for different days of a regimen that specifies different dosage amounts between the first day and the second through fifth days. Such dosage regimens are common, for example, in certain antibiotic treatment regimens.

Although not shown in FIG. 10, the instruction indicia 419 can include any other suitable characteristic of the patient to be considered when setting the dosage (e.g., the patient's height, age, target body weight, body mass index, test results, blood sugar range, and/or a severity index associated with a disease or condition), and can also include alignment marks or arrows.

In some embodiments, the syringe body 410 (or any of the syringe bodies shown and described herein) includes an opaque (or semi-opaque) label (not shown in FIG. 10) that is coupled to at least a portion of the syringe body 410. The opaque label can define an opening that is aligned with and/or that defines the first transparent window 416 and/or the second transparent window 417. In such embodiments, the opaque label can include the instruction indicia 419 and/or markings to highlight and/or "frame" the first transparent window 416 and/or the second transparent window 417.

The first transparent window 416 and/or the second transparent window 417 can be of any suitable size and/or shape to allow visual access to the indicia 446. Thus, although the first transparent window 416 and the second transparent window 417 are shown as being rectangular, in other embodiments, the first transparent window 416 and/or the second transparent window 417 (and any of the transparent windows shown and described herein) can be any shape, such circular, triangular, elliptical or the like. In some embodiments, the first transparent window 416 and/or the second transparent window 417 are sized such that only one indicia from the set of indicia 446 is visible through the respective transparent window at a time.

The plunger 440 includes a proximal end portion 442 and a distal end portion (not labeled in FIG. 10) that moves within the interior volume 418 the syringe body 410 to convey a medicament. More particularly, as described in more detail below, the plunger 440 can reciprocate along its longitudinal axis within the syringe body 410 to convey the medicament into the volume 418 (to set a dosage), and convey the medicament out of the volume 418 (to deliver the dosage). In some embodiments, the distal end portion of the plunger 440 includes an elastomeric member defining a fluid-tight (or substantially fluid-tight) seal with the side wall of the syringe body 410.

An outer surface of the plunger 440 includes at least one indicia 446 (identified as XXX). As shown, the indicia 446 is visible through each of the first transparent window 416 and the second transparent window 417 of the syringe body 410. In this manner, the indicia 446 can provide a visual indication of the dosage of medicament drawn into the syringe body 410. More specifically, because the indicia 446 is in a fixed position on the plunger 440 and each of the first transparent window 416 and the second transparent window 417 is in a fixed position on the syringe body 410, the position of the plunger 440 within the syringe body 410 at which the indicia 446 is visible via the respective transparent window corresponds to a particular volume (i.e., dosage volume) within the syringe body 410. In some embodiments, however, the indicia 446 can be non-volumetric indicia that correspond to a characteristic of the patient. For example, in some embodiments, the indicia 446 can correspond to a weight, height, age, target body weight, and/or body mass index (BMI) of the patient. In other embodiments, the indicia 446 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

In use, the plunger 440 can be reciprocated within the syringe body 410 along the longitudinal axis to convey a medicament into and/or out of the internal volume 418 of the syringe body 410. To prepare a dose of the medicament for delivery on the first day of the regimen, the delivery tip 432 is placed in fluid communication with a source of medicament (e.g., a medicament container, not shown in FIG. 10), and the plunger 440 is moved proximally to draw the medicament into the syringe body 410. The plunger 440 is moved proximally until the indicia 446 (the indicia "XXX") is visible through the first transparent window 416. In this manner, the syringe assembly 400 is placed in its second (or "day 113 dosage set") configuration. The indicia 446 (indicated as "XXX") can be, for example, a non-volumetric indicia (e.g., a weight range, a height range and/or an age range of the patient). In this manner, the user can easily set the desired dosage for a particular day of a regimen by withdrawing the plunger 440 until the indicia 446 (the indicia "XXX") is visible within the desired transparent window. This arrangement allows the dosage to be set without the need for calculation, conversion or consideration of the patient's characteristics to a volumetric measurement.

To deliver the dosage withdrawn, the user then places the delivery tip 432 in the desired location (e.g., in the patient's mouth) and moves the plunger 440 distally. The movement of the distal end portion of the plunger 440 within the syringe body 410 decreases the internal volume 418, which, in turn, produces a pressure that conveys the medicament out of the syringe body 410.

To prepare a dose of the medicament for delivery on the second through fifth days of the regimen, the delivery tip 432 is again placed in fluid communication with the source of medicament, and the plunger 440 is moved proximally to draw the medicament into the syringe body 410. The plunger 440 is moved proximally until the indicia 446 (the indicia "XXX") is visible through the second transparent window 417. In this manner, the syringe assembly 400 is placed in its second (or "days 2-5—dosage set") configuration. The dosage can then be delivered as described above.

Although the syringe body 410 is described as including at least two transparent windows arranged coaxially along a longitudinal axis, in other embodiments, a syringe body can include any number of transparent windows arranged in any manner along the syringe body. For example, FIGS. 11 and 12 show a syringe assembly 500 that includes a plunger 540, a syringe body 510 having multiple transparent windows, and a series of removable labels. The syringe body 510 includes a proximal end portion 512 and a distal end portion 514. The distal end portion 514 includes a delivery tip 532, which can be any suitable tip or member through which the medicament can be conveyed either into or out of the syringe body 510. In some embodiments, the delivery tip 532 can be a protrusion extending from the syringe body 510 that can be received within a medicament container (e.g., bottle, vial or the like) and that can also deliver the medicament orally to the patient. In other embodiments, the delivery tip 532 can a tapered fitting (such as a Luer fitting) that is adapted to couple the distal end portion 514 of the syringe body 510 to a needle (not shown).

The syringe body 510 includes a first transparent window 516, a second transparent window 517, and a third transparent window 518 (which is covered by the removable label 530). The first transparent window 516, the second transparent window 517, and the third transparent window 518 are positioned offset from each other along the longitudinal axis of the syringe body 510. Moreover, each of the transparent windows is positioned such that at least one indicia 546 on the plunger 540 is visible therethrough when the plunger 540 is in a particular longitudinal position within the syringe body 510 (i.e., at a position that corresponds to a dosage). Although FIG. 12 only shows one indicia 546, which is visible via the second transparent window 517, the plunger 540 includes a series of indicia 546 (not shown) that are radially aligned with each of the first transparent window 516 and the third transparent window 518.

As shown, the outer surface of the syringe body 510 also includes a series of instruction indicia 519. At least portion of the instruction indicia 519 are specific to and/or unique to each of the first transparent window 516, the second transparent window 517, and the third transparent window 518. More specifically, the first transparent window 516 is adjacent to, framed by and/or associated with the instruction indicia 519 indicating "DAY 1" and "LB" and the second transparent window 517 is adjacent to, framed by and/or associated with the instruction indicia 519 indicating "DAY 2" and "LB" (portions of "DAY 2" are not shown in FIG. 12). As described in more detail below, this arrangement allows the syringe assembly 500 to easily identify the dosage of a drug for different days of a regimen. Although not shown in FIGS. 11 and 12, the instruction indicia 519 can include any other suitable characteristic of the patient to be considered when setting the dosage (e.g., the patient's height, age, target body weight, body mass index, blood sugar range and/or a severity index associated with a disease or condition), and can also include alignment marks or arrows.

In some embodiments, the syringe body 510 (or any of the syringe bodies shown and described herein) includes an opaque (or semi-opaque) label (not shown in FIGS. 11 and 12) that is coupled to at least a portion of the syringe body 510. The opaque label can define an opening that is aligned with and/or that defines the first transparent window 516, the second transparent window 517, and/or the third transparent window 518. In such embodiments, the opaque label can include the instruction indicia 519 and/or markings to highlight and/or "frame" the first transparent window 516 and/or the second transparent window 517. The opaque label can also surround only a portion of the syringe body 510, thereby allowing a portion of the syringe body 510 to remain transparent (e.g., for viewing the medicament within the syringe body 510).

The first transparent window 516, the second transparent window 517, and/or the third transparent window 518 can be of any suitable size and/or shape to allow visual access to the indicia 546. Thus, although the first transparent window 516, the second transparent window 517, and the third transparent window 518 are shown as being rectangular, in other embodiments, the first transparent window 516, the second transparent window 517, and/or the third transparent window 518 (and any of the transparent windows shown and described herein) can be any shape, such circular, triangular, elliptical or the like. In some embodiments, the first transparent window 516, the second transparent window 517, and/or the third transparent window 518 are sized such that only one indicia from the set of indicia 546 is visible through the respective transparent window at a time.

As shown in FIG. 11, each of the transparent windows is initially covered by a removable label. More particularly, the first transparent window 516 is covered by a first removable label 528, the second transparent window 517 is covered by a second removable label 529, and the third transparent window 518 is covered by a third removable label 530. Each of the removable labels includes a unique instruction indicia (e.g., "Day 1," "Day 2," and "Day 3"). Each of the removable labels can be attached to the syringe body 510 (and/or any opaque label coupled thereto) by any suitable mechanism, such as, for example, by an adhesive, a perforated joint, or the like.

The plunger 540 includes a proximal end portion 542 and a distal end portion (not labeled in FIGS. 11 and 12) that moves within the syringe body 510 to convey a medicament. More particularly, as described in more detail below, the plunger 540 can reciprocate along its longitudinal axis within the syringe body 510 to convey the medicament into the syringe body 510 (to set a dosage), and convey the medicament out of the syringe body 510 (to deliver the dosage). In some embodiments, the distal end portion of the plunger 540 includes an elastomeric member defining a fluid-tight (or substantially fluid-tight) seal with the side wall of the syringe body 510.

The outer surface of the plunger 540 includes a series of indicia 546 (only one indicia, identified as XX, is shown in FIG. 12). As shown, at least a subset of the indicia 546 is visible through the first transparent window 516, the second transparent window 517, and the third transparent window 518. For example, in some embodiments, the plunger 540 can include three different subsets of indicia 546 that are spaced longitudinally and/or radially apart from each other. Each of the three subsets of indicia can be longitudinally and/or radially aligned with a corresponding transparent window. In this manner, the indicia 546 can provide a visual indication of the dosage of medicament drawn into the syringe body 510 for each specific day of a therapeutic regimen. More specifically, each indicia 546 is in a fixed position on the plunger 540, and each of the first transparent window 516, the second transparent window 517, and the third transparent window 518 is in a fixed position on the syringe body 510, the position of the plunger 540 within the syringe body 510 at which the indicia 546 is visible via the respective transparent window corresponds to a particular volume (i.e., dosage volume) within the syringe body 510. In some embodiments, the indicia 546 can be non-volumetric indicia that correspond to a characteristic of the patient. For example, in some embodiments, the indicia 446 can correspond to a weight, height, age, target body weight, and/or body mass index (BMI) of the patient. In other embodiments, the indicia 446 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

In use, the plunger 540 can be reciprocated within the syringe body 510 along the longitudinal axis to convey a medicament into and/or out of the internal volume 518 of the syringe body 510. To prepare a dose of the medicament for delivery on the first day of the regimen, the first removable label 528 is removed from the syringe body 510, as shown by the arrow EE in FIG. 11. The indicia on the first removable label 528 ("Day 1") provides a reminder to the user that the current dosage to be administered is the first day dosage. After the first removable label 528 is removed, the first transparent window 516 is visible to allow for convenient dosing of the "Day 1" medicament.

The delivery tip 532 is placed in fluid communication with a source of medicament (e.g., a medicament container, not shown in FIGS. 11 and 12), and the plunger 540 is moved proximally to draw the medicament into the syringe body 510. The plunger 540 is moved proximally until the desired indicia 546 is visible through the first transparent window 516. In this manner, the syringe assembly 500 is placed in its second (or "day 1—dosage set") configuration (this configuration is not shown in FIGS. 11 and 12). The indicia 546 can be, for example, a non-volumetric indicia (e.g., the patient's height, age, target body weight, body mass index, blood sugar range and/or a severity index associated with a disease or condition). In this manner, the user can easily set the desired dosage for the first day of a regimen by withdrawing the plunger 540 until the desired indicia 546 is visible within the desired transparent window. To deliver the dosage withdrawn, the user then places the delivery tip 532 in the desired location (e.g., in the patient's mouth) and moves the plunger 540 distally. The movement of the distal end portion of the plunger 540 within the syringe body 510 decreases the internal volume 518, which, in turn, produces a pressure that conveys the medicament out of the syringe body 510.

To prepare a dose of the medicament for delivery on the second day of the regimen, the second removable label 529 is removed from the syringe body 510. The indicia on the second removable label 529 ("Day 2") provides a reminder to the user that the current dosage to be administered is the second day dosage. After the second removable label 529 is removed, the second transparent window 517 is visible. The delivery tip 532 is again placed in fluid communication with the source of medicament, and the plunger 540 is moved proximally to draw the medicament into the syringe body 510. The plunger 540 is moved proximally until the desired indicia 546 (the indicia "XX" as shown in FIG. 12) is visible through the second transparent window 517. In this manner, the syringe assembly 500 is placed in its third (or "day 2—dosage set") configuration, as shown in FIG. 12. The dosage can then be delivered as described above.

This process is repeated for the third day dosage. Upon removal of the third (or last) removable label 530 and delivery of the third day dosage, the user can then discard the syringe assembly 500. In some embodiments, the syringe body 510 can include an instruction indicia that is revealed after removal of the third removable label 530 instructing the user to discard the syringe assembly 500. Although the syringe body 510 is shown as including only three transparent windows, in other embodiments, a syringe body can include any number of transparent windows and/or removable labels corresponding to any number of dosages, delivery days or the like.

In some embodiments, a syringe assembly can be used in conjunction with different medicaments. Similarly stated, in some embodiments, a syringe assembly can include multiple sets of indicia, each of which corresponds to a different "scale" or dosage setting for a different drug. For example, FIG. 13 shows a syringe assembly 600 that includes a plunger 640 and a syringe body 610 having two transparent windows, each corresponding to a different drug. The syringe body 610 includes a proximal end portion 612 and a distal end portion 614. The distal end portion 614 includes a delivery tip 632, which can be any suitable tip or member through which the medicament can be conveyed either into or out of the syringe body 610. In some embodiments, the delivery tip 632 can be a protrusion extending from the syringe body 610 that can be received within a medicament container (e.g., bottle, vial or the like) and that can also deliver the medicament orally to the patient. In other embodiments, the delivery tip 632 can a tapered fitting (such as a Luer fitting) that is adapted to couple the distal end portion 614 of the syringe body 610 to a needle (not shown).

The syringe body 610 includes a first transparent window 616 and a second transparent window 617. The first transparent window 616 and the second transparent window 617 are positioned offset from each other along the longitudinal axis of the syringe body 610, and each correspond to a different drug. Specifically, the first transparent window 616 corresponds to "Drug 1" and the second transparent window 617 corresponds to "Drug 2." Moreover, the first transparent window 616 is positioned such that at least one indicia from the first set of indicia 646 (indicia W, X, Y and Z) on the plunger 640 is visible therethrough when the plunger 640 is in a particular longitudinal position within the syringe body 610 (i.e., at a position that corresponds to a dosage). The second transparent window 617 is positioned such that at least one indicia from the second set of indicia 649 (indicia A, B and C) on the plunger 640 is visible therethrough when the plunger 640 is in a particular longitudinal position within the syringe body 610 (i.e., at a position that corresponds to a dosage).

As shown, the outer surface of the syringe body 610 also includes a series of instruction indicia 619. At least portion of the instruction indicia 619 are specific to and/or unique to each of the first transparent window 616 and the second transparent window 617. More specifically, the first transparent window 616 is adjacent to, framed by and/or associated with the instruction indicia 619 indicating "Drug 1" and "Weight" and the second transparent window 617 is adjacent to, framed by and/or associated with the instruction indicia 619 indicating "Drug 2" and "Weight." This arrangement allows the syringe assembly 600 to easily identify the dosage for different drugs. Although not shown in FIG. 13, the instruction indicia 619 can include any other suitable characteristic of the patient to be considered when setting the dosage (e.g., the patient's height, age, target body weight, body mass index, blood sugar range and/or a severity index associated with a disease or condition), and can also include alignment marks or arrows.

In some embodiments, the syringe body 610 (or any of the syringe bodies shown and described herein) includes an opaque (or semi-opaque) label (not shown in FIG. 13) that is coupled to at least a portion of the syringe body 610. The opaque label can define an opening that is aligned with and/or that defines the first transparent window 616 and/or the second transparent window 617. In such embodiments, the opaque label can include the instruction indicia 619 and/or markings to highlight and/or "frame" the first transparent window 616 and/or the second transparent window 617. The opaque label can also surround only a portion of the syringe body 610, thereby allowing a portion of the syringe body 610 to remain transparent (e.g., for viewing the medicament within the syringe body 610).

The first transparent window 616 and/or the second transparent window 617 can be of any suitable size and/or shape to allow visual access to the first set of indicia 646 and/or the second set of indicia 649, respectively. Thus, although the first transparent window 616 and the second transparent window 617 are shown as being rectangular, in other embodiments, the first transparent window 616 and/or the second transparent window 617 can be any shape, such circular, triangular, elliptical or the like. In some embodiments, the first transparent window 616 and/or the second transparent window 617 are sized such that only one indicia from the first set of indicia 646 and/or the second set of indicia 649, respectively, is visible through the respective transparent window at a time.

The plunger 640 includes a proximal end portion 642 and a distal end portion (not labeled in FIG. 13) that moves within the syringe body 610 to convey a medicament. The proximal end portion 642 of the plunger 640 includes an actuation flange 652 that can be grasped and/or manipulated by a user to move the plunger 640 within the syringe body 610. As described herein, the plunger 640 can reciprocate along its longitudinal axis $L_A$ within the syringe body 610 to convey the medicament into the syringe body 610 (to set a dosage), and convey the medicament out of the syringe body 610 (to deliver the dosage). The distal end portion of the plunger 640 includes an elastomeric member 658 defining a fluid-tight (or substantially fluid-tight) seal with the side wall of the syringe body 610.

The outer surface of the plunger 640 includes the first series of indicia 646 (identified as W, X, Y and Z) and the second series of indicia 649 (identified as A, B and C). As shown, the first series of indicia 646 correspond to dosages of the first drug, and are visible through the first transparent window 616. The second set of indicia 649 correspond to dosages of the second drug, and are visible through the second transparent window 617. As shown, the first series of indicia 646 is longitudinally and/or radially offset from the second series of indicia 649.

In use, the first series of indicia 646 can provide a visual indication of the dosage of medicament drawn into the syringe body 610 for the first drug, and the second series of indicia 649 can provide a visual indication of the dosage of medicament drawn into the syringe body 610 for the second drug. More specifically, each indicia from the first series indicia 646 is in a fixed position on the plunger 640, and the first transparent window 616 is in a fixed position on the syringe body 610. Thus, the position of the plunger 640 within the syringe body 610 at which the one of the first series of indicia 646 is visible via the first transparent window 616 corresponds to a particular volume (i.e., dosage volume) of the first drug within the syringe body 610. Similarly, each indicia from the second series indicia 649 is in a fixed position on the plunger 640, and the second transparent window 617 is in a fixed position on the syringe body 610. Thus, the position of the plunger 640 within the syringe body 610 at which the one of the second series of indicia 649 is visible via the second transparent window 617 corresponds to a particular volume (i.e., dosage volume) of the second drug within the syringe body 610

In some embodiments, the indicia 646, 649 can be non-volumetric indicia that correspond to a characteristic of the patient. For example, in some embodiments, the indicia 646, 649 can correspond to a weight, height, age, target body weight, and/or body mass index (BMI) of the patient. In other embodiments, the indicia 646, 649 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

Figure 14:
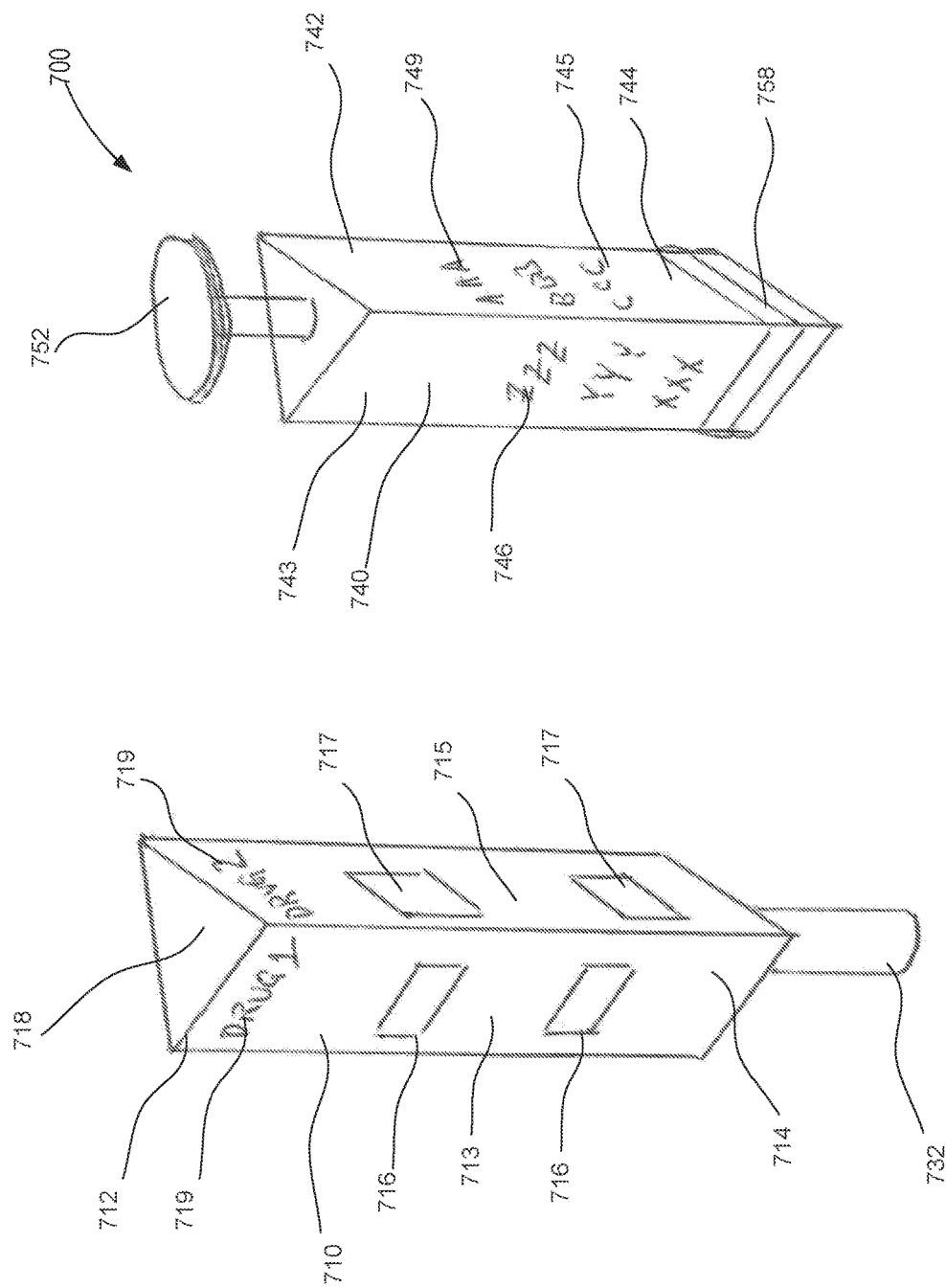
FIG. 14 is a front perspective view of the components of a syringe assembly according to an embodiment.

In some embodiments, a plunger and/or a syringe barrel can have a non-circular cross-sectional shape. In this manner, a dosage for a first drug (or day of a regimen) can be displayed on one side of a syringe assembly, and a dosage for a second drug (or day of a regimen) can be displayed on a second side of a syringe assembly. For example, FIG. 14 shows a syringe assembly 700 that includes a plunger 740 and a syringe body 710 having a triangular cross-sectional shape. The syringe body 710 includes a proximal end portion 712 and a distal end portion 714. The distal end portion 714 includes a delivery tip 732, which can be any suitable tip or member through which the medicament can be conveyed either into or out of the syringe body 710. In some embodiments, the delivery tip 732 can be a protrusion extending from the syringe body 710 that can be received within a medicament container (e.g., bottle, vial or the like) and that can also deliver the medicament orally to the patient. In other embodiments, the delivery tip 732 can a tapered fitting (such as a Luer fitting) that is adapted to couple the distal end portion 714 of the syringe body 710 to a needle (not shown).

The syringe body 710 includes a first set of transparent windows 716 and a second set of transparent windows 717. The first set of transparent windows 716 is positioned on a first side 713 of the syringe body 710, and the second set of transparent windows 717 is positioned on a second side 715 of the syringe body 710. Although not shown in FIG. 14, the third side of the syringe body 710 can include a third set of transparent windows, can be fully transparent, or opaque (fully opaque, semi-opaque or otherwise configured to disrupt the clarity of viewing objects therein). Each of the sets of transparent windows can correspond to a different drug, a different dosing regimen, or the like. Specifically, the first set of transparent windows 716 corresponds to "Drug 1" and the second set of transparent windows 717 corresponds to "Drug 2." Moreover, the first set of transparent windows 716 is positioned such that at least one indicia from the first set of indicia 746 (indicia XXX, YYY, and ZZZ) on the plunger 740 is visible through at least one of the first set of transparent windows 716 when the plunger 740 is in a particular longitudinal position within the syringe body 710 (i.e., at a position that corresponds to a dosage). The second set of transparent window 717 is positioned such that at least one indicia from the second set of indicia 749 (indicia AAA, BBB and CCC) on the plunger 740 is visible through at least one of the second set of transparent windows 719 when the plunger 740 is in a particular longitudinal position within the syringe body 710 (i.e., at a position that corresponds to a dosage).

As shown, the outer surface of the syringe body 710 also includes a series of instruction indicia 719. At least portion of the instruction indicia 719 are specific to and/or unique to each of the first set of transparent windows 716 and the second set of transparent windows 717. More specifically, the first set of transparent windows 716 is adjacent to, framed by and/or associated with the instruction indicia 719 indicating "Drug 1" and the second set of transparent windows 717 is adjacent to, framed by and/or associated with the instruction indicia 719 indicating "Drug 2." This arrangement allows the syringe assembly 700 to easily identify the dosage for different drugs.

The plunger 740 includes a proximal end portion 742 and a distal end portion (not labeled in FIG. 13) that moves within the syringe body 710 to convey a medicament. The proximal end portion 742 of the plunger 740 includes an actuation flange 752 that can be grasped and/or manipulated by a user to move the plunger 740 within the syringe body 710. As described herein, the plunger 740 can reciprocate along its longitudinal axis within the syringe body 710 to convey the medicament into the syringe body 710 (to set a dosage), and convey the medicament out of the syringe body 710 (to deliver the dosage). The distal end portion of the plunger 740 includes an elastomeric member 758 defining a fluid-tight (or substantially fluid-tight) seal with the side wall of the syringe body 710.

As shown, the plunger 740 has a triangular cross-sectional shape that corresponds to that of the syringe body 710. The non-circular cross-sectional shape of the plunger 740 limits rotation of the plunger about a longitudinal axis of the plunger 740. A first side 743 of the plunger 740 includes the first series of indicia 746 (identified as XXX, YYY and ZZZ) and a second side 745 of the plunger 740 includes the second series of indicia 749 (identified as AAA, BBB and CCC). As shown, the first series of indicia 746 correspond to dosages of the first drug, and are visible through at least one window from the first set of transparent windows 716. The second set of indicia 749 correspond to dosages of the second drug, and are visible through at least one window from the second set of transparent windows 717.

In use, the first series of indicia 746 can provide a visual indication of the dosage of medicament drawn into the syringe body 710 for the first drug, and the second series of indicia 749 can provide a visual indication of the dosage of medicament drawn into the syringe body 710 for the second drug. More specifically, each indicia from the first series indicia 746 is in a fixed position on the plunger 740, and the first transparent window 716 is in a fixed position on the syringe body 710. Thus, the position of the plunger 740 within the syringe body 710 at which the one of the first series of indicia 746 is visible via the first transparent window 716 corresponds to a particular volume (i.e., dosage volume) of the first drug within the syringe body 710. Similarly, each indicia from the second series indicia 749 is in a fixed position on the plunger 740, and the second transparent window 717 is in a fixed position on the syringe body 710. Thus, the position of the plunger 740 within the syringe body 710 at which the one of the second series of indicia 749 is visible via the second transparent window 717 corresponds to a particular volume (i.e., dosage volume) of the second drug within the syringe body 710

In some embodiments, the indicia 746, 749 can be non-volumetric indicia that correspond to a characteristic of the patient. For example, in some embodiments, the indicia 746, 749 can correspond to a weight, height, age, target body weight, and/or body mass index (BMI) of the patient. In other embodiments, the indicia 746, 749 can correspond to a test result associated with the patient, including, for example, a range of blood sugar (e.g., for insulin dosage) or any other suitable test result. In this manner, a user can withdraw a dosage of medicament without the need for calculation or conversion to determine the volumetric amount.

Figure 15:
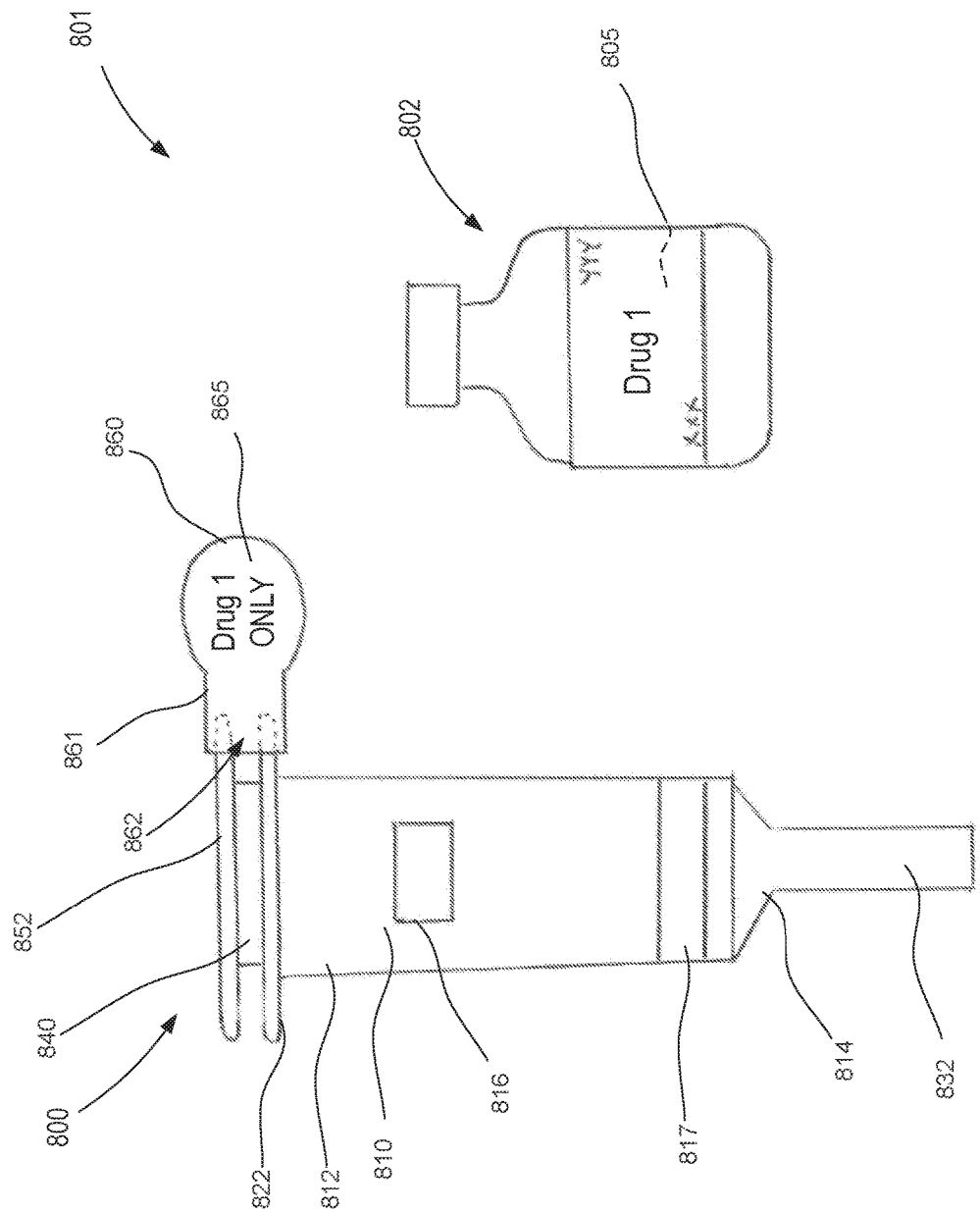
FIG. 15 is a schematic illustration of a kit including a syringe assembly and a lock member according to an embodiment.

In some embodiments, any of the syringe assemblies described herein can be included within a kit that also contains a medicament container, a lock member, a deliver member (e.g. a needle, an oral delivery tip, or the like) associated packaging and/or an instruction set. For example, FIG. 15 is a schematic illustration of a kit 801 according to an embodiment that includes a syringe assembly 800 and a medicament container 802. The syringe assembly 800 can be similar to any of the syringe assemblies shown and described herein. Accordingly, the structure of the syringe assembly 800 (including any engagement portions, transparent windows, indicia, or the like) is not described in detail below.

As shown, the syringe assembly 800 includes a syringe body 810 and a plunger 840. The syringe body 810 is configured to contain a medicament (e.g., medicament 805 from the medicament container 802), and includes a proximal end portion 812 and a distal end portion. The proximal end portion 812 includes a flange, which can be similar to any of the flanges shown and described herein (e.g., the flange 222, the flange 322 or any other flanges). The distal end portion 814 of the syringe body 810 includes a delivery tip 832, which can be similar to any of the delivery tips shown and described herein. In some embodiments, the delivery tip 832 can be a separate piece that is attached to the distal end portion 814 of the syringe body 810. In such embodiments, the kit 801 can include multiple different tips (e.g., for use on different days of a regimen, for use with different delivery conditions or the like).

The syringe body 810 includes a first transparent window 816 and a second transparent window. As described with reference to the other syringe bodies disclosed herein, the first transparent window 816 is positioned such that at least one indicia (not shown in FIG. 15) on the plunger 840 is visible therethrough. The first transparent window 816 can be of any suitable size and/or shape to allow visual access to the indicia. The second transparent window 817 is positioned distally from the first transparent window 816, and can allow the user to view the medicament within the syringe body 810 after a dose has been set. In some embodiments, for example, the second transparent window 817 extends around the entire circumference of the syringe body 810.

In some embodiments, the syringe body 810 includes an opaque (or semi-opaque) portion or label (not shown in FIG. 15) that is coupled to at least a portion of the syringe body 810. The opaque label can define an opening that is aligned with and/or that defines the first transparent window 816 and/or the second transparent window 817. In such embodiments, the opaque label can include markings to highlight and/or "frame" the first transparent window 816 and/or the second transparent window 817. Moreover, the opaque label can include instructions or other indicia associated with the medicament, therapeutic regimen or the like. For example, in some embodiments, an opaque label can include markings such as "weight," "day 1," and/or the drug name.

The plunger 840 includes a distal end portion configured to move within the syringe body 810 to convey a medicament 805. More particularly, the distal end portion 844 can reciprocate within the syringe body 810 along the longitudinal axis to convey the medicament 805 into the syringe body 810 (to set a dosage), and convey the medicament 805 out of the syringe body 810 (to deliver the dosage). A proximal end portion of the plunger 840 includes an actuation flange 852 that can be grasped and/or manipulated by a user to move the plunger 840 within the syringe body 810 to set and deliver a dose of the medicament 805, as described herein.

The syringe assembly 800 includes a lock member 860 that is removably coupled to the syringe body 810 and the plunger 840, and that limits movement of the plunger 840 within and/or with respect to the syringe body 810. In this manner, the lock member 860 can prevent the user from actuating or using the syringe assembly 800. This arrangement can be useful to provide instructions to the user regarding the particular drug or drugs with which the syringe assembly can be used. Said another way, the lock member 860 can reduce the likelihood that a user will improperly use the syringe assembly 800 to administer a drug for which it is not intended.

As shown, the lock member 860 includes a retention portion 861 that defines an opening 862. The opening 862 is configured to receive a portion of the flange 822 of the syringe body 810 and the actuation flange 852 of the plunger 840 to limit movement of the plunger 840 with respect to the syringe body 810. In some embodiments, the retention portion 861 is configured to produce an interference fit with the flange 822 and the activation flange 852 when the syringe assembly 800 is in a "ready" (or first) configuration. The lock member 860 also includes an instruction indicia 865 ("Drug 1 ONLY") that warns the user regarding the drugs and/or regimens for which the syringe assembly 800 should be used.

To prepare a dose of the medicament 805 for delivery, the cap is removed from the medicament container 802, and the lock member 860 is removed from the flange 822 and activation flange 852. The delivery tip 832 is placed into the medicament container 802, and the plunger 840 is moved proximally. The proximal movement of the distal end portion of the plunger 840 within the syringe body 810 produces a vacuum that draws the medicament 805 from the container 802 into the syringe body 810. The plunger 840 is moved proximally until an indicia on the plunger (not shown) is visible through the first transparent window 816. In this manner, the syringe assembly 800 is placed in its second (or "dosage set") configuration.

When the syringe assembly 800 is in the second configuration, the medicament within the syringe body 810 can be visually inspected via the second transparent window 817. To deliver the dosage withdrawn, the user then places the delivery tip 832 in the desired location (e.g., in the patient's mouth) and moves the plunger 840 distally, as described herein. The movement of the distal end portion 844 of the plunger 840 within the syringe body 810 produces a pressure that conveys the medicament 805 out of the syringe body.

Figure 16:
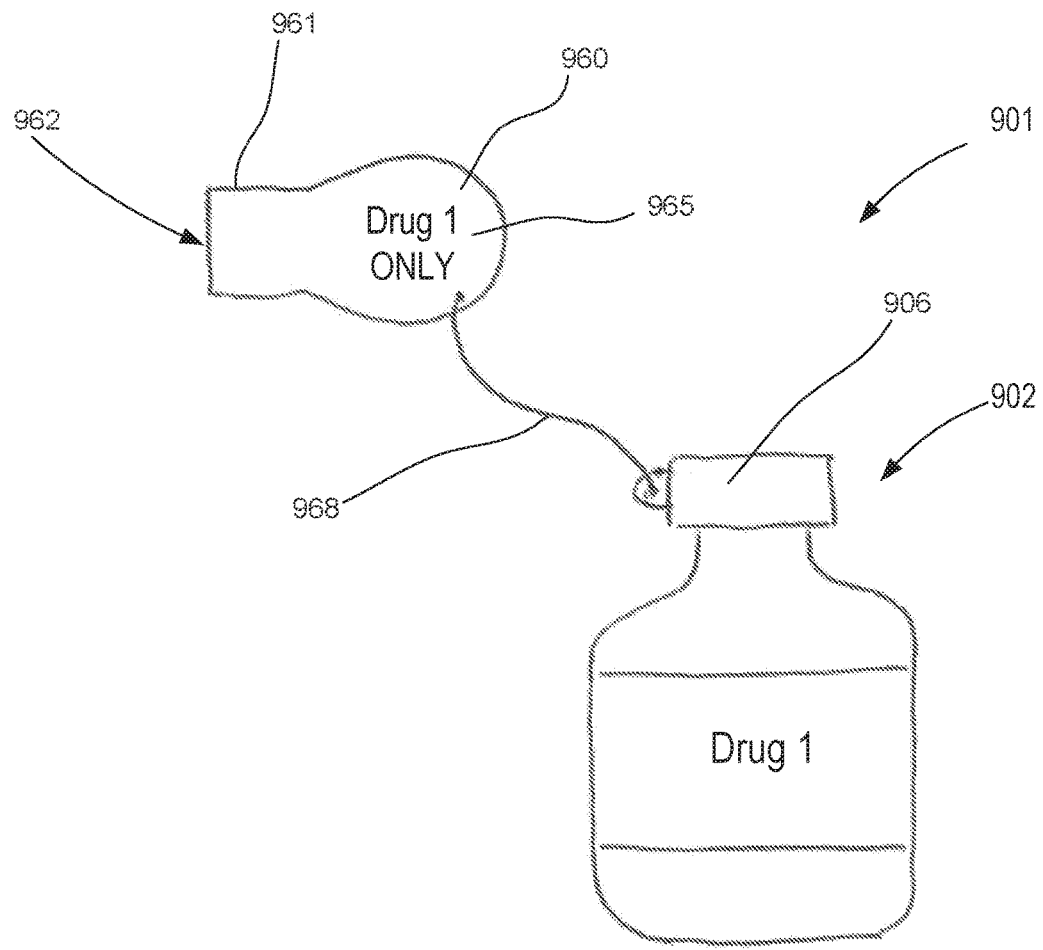
FIG. 16 is a schematic illustration of a portion of a kit including a lock member according to an embodiment.

In some embodiments, a kit can include features to reduce the likelihood that the syringe assembly therein will be used with a drug for which the assembly is not intended. For example, in some embodiments, a kit can include a coupling member that retains the syringe assembly to the medicament container. FIG. 16 shows a portion of a kit 901 according to an embodiment that includes a syringe assembly (not shown), a medicament container 902, and a lock member 960. The syringe assembly can be similar to any of the syringe assemblies shown and described herein. Accordingly, the structure of the syringe assembly (including any engagement portions, transparent windows, indicia, or the like) is not described below. The medicament container 902 contains a medicament and includes a removable cap 906.

The lock member 960 can be removably coupled to the syringe assembly to limit actuation of the syringe assembly (e.g., movement of a plunger within a syringe body). In this manner, the lock member 960 can prevent the user from actuating or using the syringe assembly when the lock member 960 is in place. As shown, the lock member 960 includes a retention portion 961 that defines an opening 962. The opening 962 is configured to receive a portion of the syringe assembly to limit and/or prevent actuation of the syringe assembly. In some embodiments, the retention portion 961 is configured to produce an interference fit with portions of the syringe assembly when the syringe assembly is in a "ready" (or first) configuration. The lock member 960 also includes an instruction indicia 965 ("Drug 1 ONLY") that warns the user regarding the drugs and/or regimens for which the syringe assembly 900 should be used.

The lock member also includes a tether 968 that is coupled to the cap 906 of the medicament container 902. In this manner, when the lock member 960 is coupled to the syringe assembly, the syringe assembly will also be attached to the medicament container 902. This arrangement maintains the syringe assembly (not shown) and the medicament container 902 in a coupled relationship, thereby reducing the likelihood that the syringe body will be improperly used (e.g., with the wrong medicament).

Although shown as including a tether 968, in other embodiments, a kit, a lock member and/or a syringe assembly can include any suitable mechanism for coupling the syringe assembly to the medicament container. For example, in some embodiments, the lock member can include a rigid, "snap fit" member that couples a syringe body to a medicament container. In other embodiments, a portion of a syringe body can also serve as the cap for a medicament container.

Figure 17A:
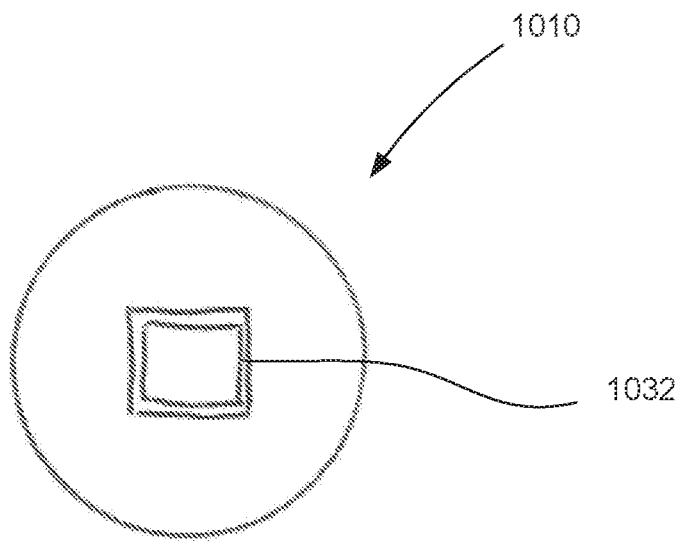
FIGS. 17A and 17B are bottom view schematic illustrations, each showing a delivery tip of a syringe assembly according to an embodiment.
Figure 17B:
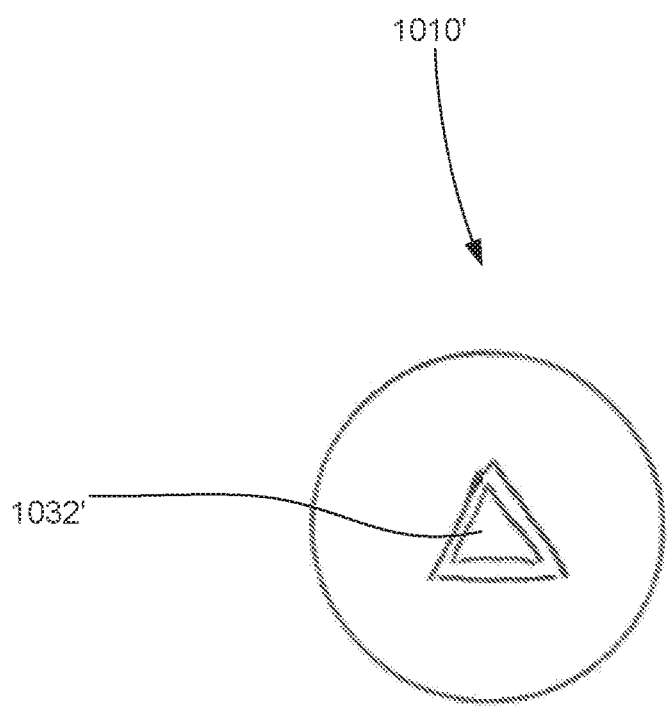

In some embodiments, a delivery tip of a syringe assembly can be uniquely configured to fit within an opening of a specific medicament container (e.g., the medicament container 802 or the medicament container 902). For example, as shown in FIGS. 17A and 17B, a delivery tip of a syringe assembly can be sized and/or shaped to fit within a corresponding opening of a medicament container. FIG. 17A shows a square-shaped delivery tip 1032 of a syringe body 1010 that is configured to fit within a corresponding square-shaped opening of a medicament container (not shown). FIG. 17B shows a triangle-shaped delivery tip 1032' of a syringe body 1010' that is configured to fit within a corresponding triangle-shaped opening of a medicament container (not shown).

Figure 18:
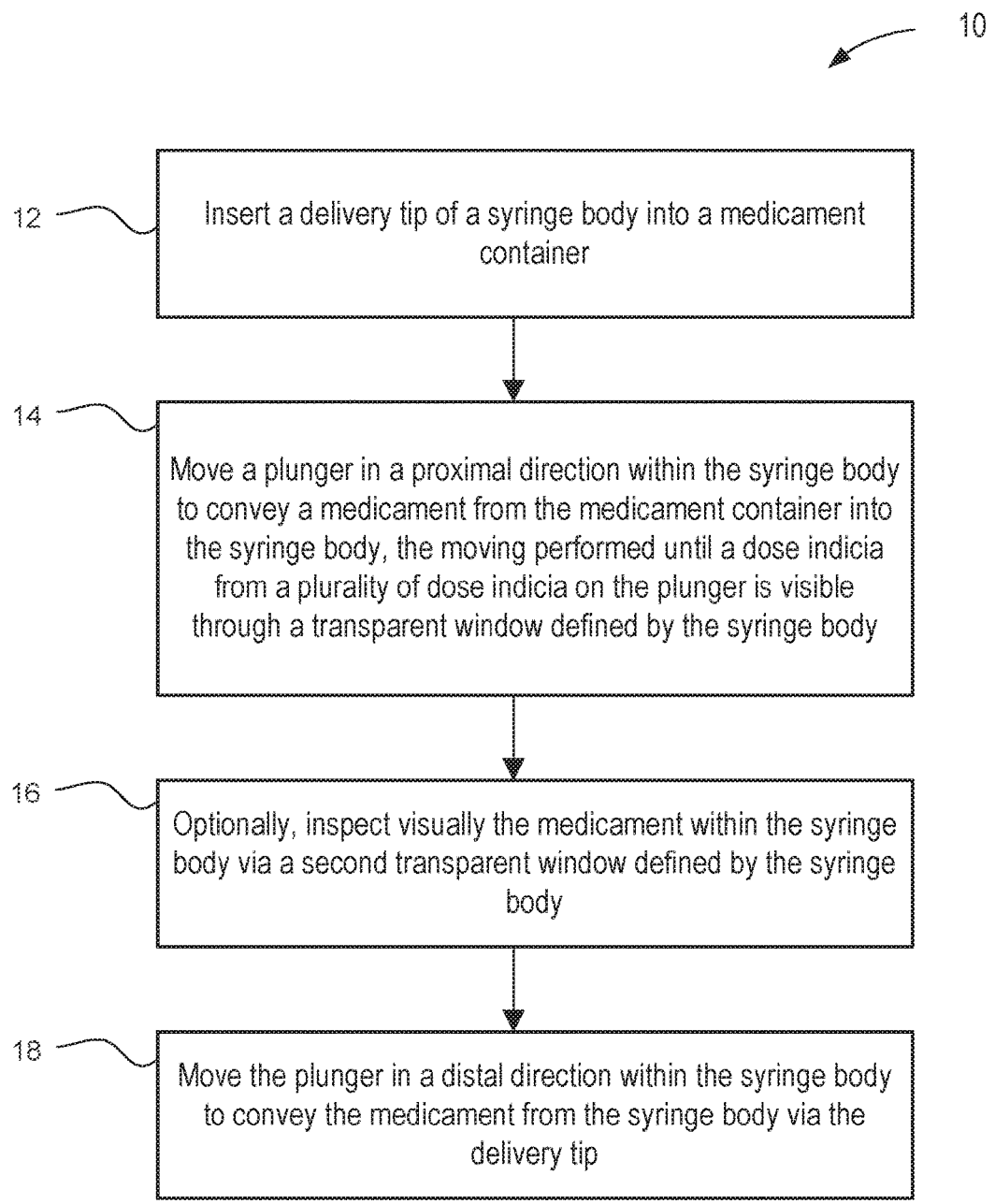
FIG. 18 is a flow chart of a method of using a syringe assembly according to an embodiment.

FIG. 18 is a flow chart illustrating a method 10 of setting a dose and delivering a medicament, according to an embodiment. The method 10 can be performed using any of the syringe assemblies or kits shown and described herein. The method includes inserting a delivery tip of a syringe body into a medicament container, at 12. The delivery tip can be, for example, an oral delivery tip (e.g., the tip 232 shown above, or any other delivery tips described herein). The medicament container can be, for example, the medicament container 902 shown and described above. In some embodiments, the delivery tip can be shaped and/or sized to fit within a corresponding opening of the medicament container. In some embodiments, the method 10 optionally includes removing a lock member, such as the lock member 860 or the lock member 960, from the delivery tip to expose the tip before it is inserted into the medicament container.

A plunger is then moved in a proximal direction within the volume of the syringe body to convey a medicament from the medicament container into the syringe body, at 14. The moving is performed until a dose indicia from a series of dose indicia on the plunger is visible through a transparent window defined by the syringe body. In some embodiments, the plunger includes an engagement portion configured to interface with an engagement portion of the syringe body to limit rotation of the plunger about a longitudinal axis of the plunger during the moving. In this manner, the series of dose indicia on the plunger remain radially aligned with the transparent window.

In some embodiments, the method optionally includes visually inspecting the dosage of medicament within the syringe body via a second transparent window defined by the syringe body, at 16. In some embodiments, the second transparent window is located distally from the first transparent window (e.g., similar to the arrangement shown in FIG. 15). In other embodiments, the second transparent window can be an entire transparent portion of a syringe body, as shown and described above with respect to the syringe body 210.

The plunger is then moved in a distal direction within the volume of the syringe body to convey the medicament from the volume via the delivery tip, at 18. In some embodiments, the method can include repeating the delivery operations multiple times (e.g., on different days and/or dose intervals).

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, any of the syringe assemblies described herein can include any suitable engagement mechanism (or mating engagement portions) to limit rotation of the plunger within the syringe body. For example, any of the syringe bodies shown and described herein can include an engagement portion similar to the engagement portion 124. Such engagement portions can include, for example, a protrusion configured to be disposed within a corresponding groove of the plunger. In other embodiments, such engagement portions can include a recessed portion configured to receive a protrusion of the plunger. In yet other embodiments, such engagement portions can include a splined surface that interfaces with a corresponding splined surface of the plunger to limit, reduce and/or prevent rotation of the plunger within the syringe body.

Any of the transparent windows shown and described herein can be of any suitable size and/or shape to allow visual access to the indicia.

Any of the plungers shown and described herein can include an elastomeric member, such as the elastomeric member 658 shown and described above. Any such elastomeric member can be constructed from any suitable material, and can be formulated to be compatible with the medicament housed within the syringe body. Similarly stated, the elastomeric member can be formulated to minimize any reduction in the efficacy of the medicament that may result from contact (either direct or indirect) between the elastomeric member and the medicament. In some embodiments, at least a portion of the elastomeric member can be coated to improve the lubricity of the elastomeric member.

Although the syringe assemblies are shown and described herein as being suitable for multiple uses (e.g., for a therapeutic regimen over several days and/or doses), in other embodiments, any of the syringe assemblies described herein can be configured for a single-use application. In this manner, the likelihood of using the syringe assembly with the wrong medicament is reduced. For example, in some embodiments, a syringe assembly can include a locking tab (e.g., on a flange of the syringe body) that engages and retains the plunger in the distal-most position after a single dose has been delivered. In other embodiments, the syringe assembly can include a frangible portion that breaks and/or permanently deforms such that the plunger cannot be repeatedly reciprocated within the syringe body.

In some embodiments, a syringe body includes a lock member configured to limit movement of the distal end portion of the plunger in a proximal direction within the syringe body after a dose of the medicament has been delivered from the volume of the syringe body.

In some embodiments, a syringe body includes a protrusion configured to engage a portion of the plunger to limit movement of the distal end portion of the plunger in a proximal direction within the syringe body when the distal end portion of the plunger is in a distal-most position within the syringe body.

Any of the devices and/or medicament containers shown and described herein can be constructed from any suitable material. Such materials include glass, plastic (including thermoplastics such as cyclic olefin copolymers), or any other material used in the manufacture of syringes containing medications.

Any of the devices and/or medicament containers shown and described herein can include and/or be used with any suitable medicament or therapeutic agent. In some embodiments, the medicament contained within any of the medicament containers and/or syringe assemblies shown herein can include acetaminophen, ibuprofen, diphenhydramine (Benadryl), cough and cold medicines, vitamins, Prescriptions: azithromycin, albuterol, allopurinol, cefdinir, chloroquine, choleystyramine, doxycycline, enoxaparin, erythromycin, hydroxychloroquine, isoniazid, levofloxacin, magnesium sulfate, methadone, omeprazole, Tamiflu, roxicet, pyridium, Compazinem Phenergan, kayexelate, prednisone, prednisolone, and/or dexamethasone.

The syringe assemblies disclosed herein can contain any suitable amount of any medicament. For example, in some embodiments, a syringe assembly as shown herein can be sized and/or can define a volume sufficient to contain any suitable dosage of medicament.

Although various embodiments have been described as having particular features and/or combinations of components, other embodiments are possible having a combination of any features and/or components from any of embodiments where appropriate. For example, any of the syringe assemblies described herein can include a detent mechanism of the types shown and described with respect to the syringe assembly 200. Specifically, any of the syringe bodies shown and described herein can include a syringe detent configured to engage one or more plunger detents to resist movement of the plunger within the syringe body when each of a series of indicia is visible through a transparent window. In this manner, the user can receive a tactile sensation (e.g., a slight snap, click or vibration) when each of the indicia are aligned with and/or visible via the transparent window. In this manner, the syringe assembly can allow for a series of discrete intervals of plunger movement within the syringe body.

Any of the kits described herein (e.g., the kit 801 and/or the kit 901) can be used with and/or include any of the syringe assemblies shown and described herein. Similarly stated, each of the kit 801 and the kit 901 can include any of the syringe assemblies 100, 200 300, 400, 500, 600, 700, 800 and/or 900, and variants thereof.

As another example, any of the syringe bodies described herein can include an opaque (or semi-opaque) label similar to that described above in conjunction with the syringe body 210.

Any of the syringe bodies described herein can include any configuration or arrangement of transparent windows described herein. For example, although the syringe body 110 is shown and described as include only a single transparent window, in other embodiments, the syringe body 110 (and any other syringe body described herein) can include multiple transparent windows as shown in connection with the syringe body 500, the syringe body 600 and/or the syringe body 700.

Any of the syringe bodies shown and described herein can include any of the flanges described herein, such as the flange 322.

What is claimed is:

1. A method of delivering a medicament, comprising:
    inserting a distal end portion of a plunger into a volume defined by a syringe body through a lateral opening defined in a flange member, the lateral opening between a proximal end portion of the flange member and a distal end portion of the flange member, the distal end portion of the plunger including an elastomeric member, the syringe body having a proximal end portion at a first end and a distal end portion at an opposite second end, the flange member coupled to the proximal end portion of the syringe body;
    inserting a delivery tip of the syringe body into a medicament container;
    moving the plunger in a proximal direction to a proximal position within the syringe body to convey the medicament from the medicament container into the volume, the moving performed until a dose indicium from a plurality of dose indicia on the plunger is visible through a transparent window defined by the syringe body when the plunger is at the proximal position, the plunger including an engagement portion configured to interface with an engagement portion of the flange member to limit rotation of the plunger about a longitudinal axis of the plunger during the moving; and
    moving the plunger in a distal direction within the volume of the syringe body through a distance between the proximal position and a distal position at the distal end portion of the syringe body to convey the medicament from the volume via the delivery tip, wherein the interface between the engagement portion of the plunger and the engagement portion of the flange member prevents rotation of the plunger about the longitudinal axis of the plunger when the plunger moves through the distance.

2. The method of claim 1, wherein the moving the plunger in the proximal direction is performed at a first time to convey a first dose of the medicament, the method further comprising:
    inserting the delivery tip of a syringe body into the medicament container at a second time; and
    moving the plunger in the proximal direction within the volume of the syringe body to convey a second dose of the medicament from the medicament container into the volume, the moving the plunger to convey the second dose performed until the dose indicium from the plurality of dose indicia on the plunger is visible through the transparent window defined by the syringe body.

3. The method of claim 1, wherein a portion of a side wall surrounding the transparent window is opaque, the transparent window being sized such that only one dose indicium from the plurality of dose indicia is visible through the transparent window at a time.

4. The method of claim 3, wherein:
    the plurality of dose indicia is arranged coaxially along the longitudinal axis of the plunger;
    the portion of the side wall includes at least one of a framing indicium or a first instruction indicium, the framing indicium at least partially surrounding the transparent window; and
    a proximal end portion of the plunger including a second instruction indicium.

5. The method of claim 1, wherein the transparent window is a first transparent window, the method further comprising:
    inspecting visually, before the moving the plunger in the distal direction, the medicament within the volume of the syringe body via a second transparent window defined by the syringe body, the second transparent window located distally from the first transparent window.

6. The method of claim 1, wherein the moving the plunger in the proximal direction is performed until a syringe detent engages a plunger detent to resist movement of the plunger within the volume of the syringe body.

7. The method of claim 1, wherein:
    the transparent window is at a first portion of a side wall of the syringe body;
    the elastomeric member defines a fluid-tight seal with a second portion of the side wall of the syringe body, the second portion of the side wall of the syringe body and the first portion of the side wall of the syringe body having a constant cross-sectional inner diameter; and
    the moving the plunger in the distal direction within the volume of the syringe body includes moving the elastomeric member in the distal direction within the constant cross-sectional inner diameter.

8. The method of claim 1, wherein:
    an opaque member is coupled to the syringe body, the opaque member defining an opening such that the opaque member frames the transparent window, at least one of the opening or the transparent window being sized such that only one dose indicium from the plurality of dose indicia is visible through the transparent window at a time; and
    the moving the plunger in the proximal direction to the proximal position includes moving the plunger until the dose indicium from the plurality of dose indicia on the plunger is visible through the opening defined by the opaque member.

9. The method of claim 8, wherein the plurality of dose indicia is arranged coaxially along the longitudinal axis of the plunger and at a constant circumferential position along an outer surface of the plunger such that each of the plurality of dose indicia is visible through the transparent window when the plunger moves within the volume of the syringe body.

10. The method of claim 1, wherein:
    the transparent window is a first transparent window;
    an opaque member disposed about a side wall of the syringe body surrounds the first transparent window;
    the side wall of the syringe body defines a second transparent window, the second transparent window located distally from the first transparent window such that the medicament within the volume of the syringe body is visible via the second transparent window when the dose indicium is visible through the first transparent window; and
    the moving the plunger in the proximal direction to the proximal position includes moving the plunger in the proximal direction until the dose indicium is visible through the first transparent window and the medicament is visible through the second transparent window.

11. The method of claim 1, wherein:
the engagement portion of the plunger extends along the longitudinal axis of the plunger; and
the moving the plunger in the distal direction includes maintaining the interface between the engagement portion of the plunger and the engagement portion of the flange member during the moving the plunger in the distal direction through the distance.

12. The method of claim 1, wherein:
the engagement portion of the flange member is a slot;
the engagement portion of the plunger is matingly received within the slot; and
the preventing the rotation of the plunger about the longitudinal axis of the plunger through the distance results from maintaining the engagement portion of the plunger within the slot when the engagement portion of the plunger moves in the distal direction through the distance.

13. A kit, comprising:
a medicament container containing a medicament, the medicament container defining an opening; and
a syringe assembly including a syringe body and a plunger, a proximal end portion of the syringe body coupled to a flange, a distal end portion of the syringe body including a delivery tip configured to be disposed within the medicament container to withdraw a dose of the medicament from the medicament container into a volume defined by the syringe body, a side wall of the syringe body including a transparent window, a distal end portion of the plunger configured to move within the volume of the syringe body and contact the medicament to convey the medicament,
the flange including a distal flange portion and a proximal flange portion, the distal flange portion coupled to the proximal end portion of the syringe body, the proximal flange portion defining a lateral opening and an engagement slot, the lateral opening having a size and extending toward the distal flange portion such that the distal end portion of the plunger can be removed from the syringe body via the lateral opening,
an engagement portion of the plunger matingly received within the engagement slot of the flange to prevent rotation of the plunger about a longitudinal axis of the plunger when the distal end portion of plunger moves through a distance between a proximal position and a distal position at the distal end portion of the syringe body, and
an outer surface of the plunger including a plurality of dose indicia, at least one indicium from the plurality of dose indicia being visible through the transparent window.

14. The kit of claim 13, wherein:
the syringe assembly includes an opaque member surrounding the transparent window of the syringe body, the opaque member defining an opening sized such that only one dose indicium from the plurality of dose indicia is visible through the transparent window at a time; and
the plurality of dose indicia is arranged coaxially along the longitudinal axis of the plunger.

15. The kit of claim 13, further comprising:
a lock member removably coupled to the proximal end portion of the syringe body and a proximal end portion of the plunger, the lock member configured to limit movement of the distal end portion of the plunger within the syringe body, the lock member including an instruction indicium.

16. The kit of claim 13, further comprising:
an opaque member coupled to the syringe body, the opaque member defining an opening such that the opaque member frames the transparent window, the opening being sized such that only one indicium from the plurality of dose indicia is visible through the transparent window at a time.

17. The kit of claim 13, wherein:
the plurality of dose indicia is arranged coaxially along the longitudinal axis of the plunger and at a constant circumferential position along the outer surface of the plunger such that each of the plurality of dose indicia is visible through the transparent window when the plunger moves within the volume of the syringe body.

18. The kit of claim 13, wherein:
the transparent window is at a first portion of the side wall of the syringe body; and
the distal end portion of the plunger including an elastomeric member defining a fluid-tight seal with a second portion of the side wall of the syringe body, the second portion of the side wall of the syringe body and the first portion of the side wall of the syringe body having a constant cross-sectional inner diameter.

19. An apparatus, comprising:
a syringe body defining a volume configured to contain a medicament, the syringe body having a proximal end portion, a side wall, and a distal end portion, the distal end portion of the syringe body including a delivery tip, the side wall including a transparent window portion;
a flange member, a distal end portion of the flange member affixed to the proximal end portion of the syringe body, a proximal end portion of the flange member including an engagement portion, the proximal end portion of the flange member defining a lateral opening between the engagement portion and the distal end portion of the flange member; and
a plunger having a distal end portion including an elastomeric member configured to define a fluid-tight seal with the side wall of the syringe body, the distal end portion of the plunger configured to move within the volume of the syringe body to convey the medicament, the distal end portion of the plunger configured to be removed from the volume of the syringe body via the lateral opening, an engagement portion of the plunger configured to interface with the engagement portion of the flange member to limit rotation of the plunger about a longitudinal axis of the plunger, an outer surface of the plunger including a plurality of indicia, at least one indicium from the plurality of indicia being visible through the transparent window portion.

20. The apparatus of claim 19, wherein:
the syringe assembly includes an opaque member surrounding the transparent window portion, the opaque member defining an opening sized such that only one dose indicium from the plurality of dose indicia is visible through the transparent window portion at a time;
the plurality of dose indicia is arranged coaxially along the longitudinal axis of the plunger; and
the engagement portion of the plunger includes a splined surface.

* * * * *